(12) United States Patent
Park et al.

(10) Patent No.: US 10,206,688 B2
(45) Date of Patent: Feb. 19, 2019

(54) ARTHROPLASTY DEVICES AND RELATED METHODS

(71) Applicant: Howmedica Osteonics Corporation, Mahwah, NJ (US)

(72) Inventors: Ilwhan Park, Walnut Creek, CA (US); Charlie W. Chi, Milpitas, CA (US)

(73) Assignee: Howmedica Osteonics Corporation, Mahwah, NJ (US)

( * ) Notice: Subject to any disclaimer, the term of this patent is extended or adjusted under 35 U.S.C. 154(b) by 0 days.

(21) Appl. No.: 15/718,850

(22) Filed: Sep. 28, 2017

(65) Prior Publication Data

US 2018/0014836 A1    Jan. 18, 2018

Related U.S. Application Data

(63) Continuation of application No. 11/642,385, filed on Dec. 19, 2006, now Pat. No. 9,808,262.
(Continued)

(51) Int. Cl.
  *A61B 17/15*    (2006.01)
  *A61B 17/17*    (2006.01)
(Continued)

(52) U.S. Cl.
  CPC .......... *A61B 17/154* (2013.01); *A61B 17/155* (2013.01); *A61B 17/157* (2013.01);
(Continued)

(58) Field of Classification Search
  CPC .... A61B 17/154; A61B 17/155; A61B 17/157
  See application file for complete search history.

(56) References Cited

U.S. PATENT DOCUMENTS 4,517,969 A * 5/1985 Halcomb ............. A61F 2/4657
                                                          33/512
5,133,758 A    7/1992 Hollister
(Continued)

FOREIGN PATENT DOCUMENTS

EP    0709061 A1    5/1996
EP    1669033 A1    6/2006
(Continued)

OTHER PUBLICATIONS

Banks et al. "Accurate Measurement of Three-Dimensional Knee Replacement Kinematics Using Single-Plane Fluoroscopy." *IEEE Transactions on Biomedical Engineering*, vol. 43, No. 6, Jun. 1996.
(Continued)

*Primary Examiner* — Christian Sevilla
(74) *Attorney, Agent, or Firm* — Polsinelli PC

(57) ABSTRACT

Arthroplasty jigs and related methods are disclosed. Some of the arthroplasty jigs may comprise a jig body that is configured to align with a surface of a bone, and a positioning component. Certain of the methods may comprise providing such an arthroplasty jig, and aligning the jig body with a surface of a bone so that the positioning component provides at least one of a visible, audible, or tactile indication that such alignment has been achieved. Some of the arthroplasty jigs may comprise a jig body that is configured to align with a surface of a bone, and that is marked with identifying information. Certain of the methods may comprise providing an arthroplasty jig comprising a jig body that is configured to align with a surface of a bone, or providing an arthroplasty jig blank, and marking the arthroplasty jig or the arthroplasty jig blank with identifying information.

23 Claims, 21 Drawing Sheets

Related U.S. Application Data

(60) Provisional application No. 60/773,491, filed on Feb. 15, 2006.

(51) Int. Cl.
*A61B 90/94* (2016.01)
*A61B 90/00* (2016.01)

(52) U.S. Cl.
CPC .......... *A61B 17/1764* (2013.01); *A61B 90/94* (2016.02); *A61B 17/1739* (2013.01); *A61B 17/1742* (2013.01); *A61B 17/1778* (2016.11); *A61B 90/06* (2016.02); *A61B 2090/036* (2016.02); *A61B 2090/068* (2016.02)

(56) References Cited

U.S. PATENT DOCUMENTS

| | | |
|---|---|---|
| 5,150,304 A | 9/1992 | Berchem |
| 5,417,694 A | 5/1995 | Marik |
| 5,454,717 A | 10/1995 | Andreiko |
| 5,514,140 A | 5/1996 | Lackey |
| 5,735,856 A | 4/1998 | McCue |
| 5,762,125 A | 6/1998 | Mastrorio |
| 6,033,415 A | 3/2000 | Mittelstadt |
| 6,132,447 A * | 10/2000 | Dorsey .............. A61B 17/3201 30/194 |
| 6,458,135 B1 * | 10/2002 | Harwin ................ A61B 17/155 606/88 |
| 6,757,582 B2 | 6/2004 | Brisson et al. |
| 7,203,628 B1 | 4/2007 | St Ville |
| 7,373,286 B2 | 5/2008 | Nikolskiy et al. |
| 7,548,638 B2 | 6/2009 | Graessner |
| 7,584,080 B2 | 9/2009 | Taylor et al. |
| 9,014,438 B2 | 4/2015 | Habets |
| 9,265,509 B2 | 2/2016 | Park et al. |
| 9,451,970 B2 | 9/2016 | Park |
| 9,549,782 B2 | 1/2017 | Park et al. |
| 9,610,086 B2 | 4/2017 | Park et al. |
| 9,636,120 B2 | 5/2017 | Park |
| 9,730,713 B2 | 8/2017 | Park et al. |
| 9,757,136 B2 | 9/2017 | Park et al. |
| 9,782,227 B2 | 10/2017 | Park et al. |
| 9,814,533 B2 | 11/2017 | Park et al. |
| 2002/0055679 A1 | 5/2002 | Sati |
| 2002/0183760 A1 | 12/2002 | McGovern |
| 2004/0260301 A1 * | 12/2004 | Lionberger .......... A61B 17/155 606/88 |
| 2005/0148843 A1 * | 7/2005 | Roose .................... A61B 17/17 600/407 |
| 2005/0234461 A1 * | 10/2005 | Burdulis, Jr. ........ A61B 17/155 606/79 |
| 2006/0093240 A1 | 5/2006 | Sabuncu et al. |
| 2006/0161167 A1 | 7/2006 | Myers |
| 2007/0038223 A1 | 2/2007 | Marquart |
| 2007/0066917 A1 | 3/2007 | Hodorek |
| 2007/0173853 A1 | 7/2007 | MacMillan |
| 2007/0237372 A1 | 10/2007 | Chen et al. |
| 2007/0270680 A1 | 11/2007 | Sheffer |
| 2008/0132783 A1 | 6/2008 | Revie et al. |
| 2008/0208081 A1 | 8/2008 | Murphy |
| 2010/0036252 A1 | 2/2010 | Chalana et al. |
| 2016/0015466 A1 | 1/2016 | Park et al. |
| 2016/0095609 A1 | 4/2016 | Park et al. |
| 2016/0213491 A1 | 7/2016 | Schoenefeld |
| 2016/0228194 A1 | 8/2016 | Park et al. |
| 2016/0228195 A1 | 8/2016 | Park et al. |
| 2016/0228196 A1 | 8/2016 | Park et al. |
| 2016/0228197 A1 | 8/2016 | Park et al. |
| 2016/0270857 A1 | 9/2016 | Park et al. |
| 2016/0310217 A1 | 10/2016 | Park et al. |
| 2017/0007275 A1 | 1/2017 | Park et al. |
| 2017/0196642 A1 | 7/2017 | Park |
| 2017/0202622 A1 | 7/2017 | Park et al. |
| 2017/0209219 A1 | 7/2017 | Park et al. |
| 2017/0209221 A1 | 7/2017 | Park et al. |
| 2018/0000497 A1 | 1/2018 | Park et al. |

FOREIGN PATENT DOCUMENTS

| | | |
|---|---|---|
| FR | 2478462 A1 | 9/1981 |
| JP | P 2005-287813 | 10/2005 |
| WO | WO 98/32384 | 7/1998 |
| WO | WO 2006/127486 A2 | 11/2006 |
| WO | WO 2007/097854 A2 | 8/2007 |
| WO | WO 2007/137327 A1 | 12/2007 |
| WO | WO 2008/014618 A1 | 2/2008 |
| WO | WO 2008/091358 A1 | 7/2008 |

OTHER PUBLICATIONS

Calvo et al., "High Resolution MRI Detects Cartilage Swelling at the Early Stages of Experimental Osteoarthritis," OARSI, 2001, pp. 463-472.

Delp et al. "An Interactive Graphics-Based Model of the lower Extremity to Study Orthopaedic Surgical Procedures." *IEEE Transactions on Biomedical Engineering*, vol. 37, No. 8, Aug. 1990.

Garg, A. et al.. "Prediction of Total Knee Motion Using a Three-Dimensional Computer-Graphics Model." *J. Biomechanics*, vol. 23, No. 1, pp. 45-58, 1990.

Richolt et al. "Planning and Evaluation of Reorienting Osteotomies of the Proximal Femur in Cases of SCFE Using Virtual Three-Dimensional Models." *Lecture Notes in Computer Science*, vol. 1496, 1998, pp. 1-8.

Taylor et al., "Computer-integrated revision total hip replacement surgery: concept and preliminary results," Medical Image Analysis (1999) vol. 3, No. 3, pp. 301-319.

Walker, P. S. et al. "Range of Motion in Total Knee Arthroplasty: A Computer Analysis." *Clinical Orthopaedics and Related Research*, No. 262, Jan. 1991.

Amendment and Response After Final Office Action, U.S. Appl. No. 11/656,323, dated Aug. 25, 2014.

Amendment Under 37 CFR 1.312, U.S. Appl. No. 14/824,731, dated Dec. 28, 2015.

Appeal Brief, U.S. Appl. No. 11/946,002, dated Oct. 13, 2016.

Australian Patent Examination Report No. 1, AU 2013200861, dated Mar. 3, 2015.

Canadian Office Action, 2721735, dated Aug. 24, 2016.

Canadian Office Action, Appl. No. 2642616, dated Apr. 22, 2015.

Canadian Office Action, Appl. No. 2708393, dated Jul. 29, 2014.

Canadian Office Action, CA2642616, dated Jan. 12, 2017.

Canadian Office Action, CA2642616, dated Feb. 26, 2016.

Canadian Office Action, CA2708393, dated Mar. 11, 2016.

Canadian Office Action, CA2708393, dated May 7, 2015.

Canadian Office Action, CA2721735, dated Jul. 7, 2015.

Canadian Office Action, CA2721762, dated Nov. 10, 2015.

Canadian Office Action, CA2721762, dated Jul. 20, 2016.

Decision on Appeal, U.S. Appl. No. 12/391,008, dated Dec. 11, 2015.

EP Communication pursuant to Article 94(3) EPC, EP10192631.9, dated Feb. 12, 2016.

EP Examination Report, EP13188389.4, dated Jan. 30, 2017.

EP Search Report and Opinion, EP09800841.0, dated Mar. 22, 2016.

EP Search Report, EP17183082.1, dated Oct. 10, 2017.

European Examination Report, EP10192631.9, dated Feb. 11, 2015.

European Patent Office, Summons to Attend Oral Proceedings, EP07749030.8, dated Sep. 10, 2015.

European Search Report, EP 09835583.7, dated May 9, 2014.

European Search Report, EP09718014.5, dated May 13, 2015.

European Search Report, EP09718041.8, dated May 12, 2015.

European Search Report, EP09823986.6, dated Sep. 23, 2014.

Examination Report, Indian App. No. 673/KOLNP/2011, dated Jun. 29, 2017.

Examiner's Answer in appeal, U.S. Appl. No. 11/946,002, dated Jan. 23, 2017.

(56) References Cited

OTHER PUBLICATIONS

Extended European Search Report, EP11769533.8, dated Jan. 9, 2017.
Extended European Search Report, European Appl. No. 13188389.4, dated Jan. 8, 2014.
Extended European Search Report, European Appl. No. 14765072.5, dated Sep. 22, 2016.
Final Office Action, U.S. Appl. No. 11/656,323, dated Apr. 3, 2014.
Final Office Action, U.S. Appl. No. 11/946,002, dated Sep. 17, 2014.
Final Office Action, U.S. Appl. No. 11/946,002, dated Nov. 30, 2015.
Final Office Action, U.S. Appl. No. 13/923,093, dated Jul. 14, 2016.
Final Office Action, U.S. Appl. No. 14/011,998, dated Jul. 14, 2016.
Final Office Action, U.S. Appl. No. 14/084,255, dated Jul. 26, 2016.
Final Office Action, U.S. Appl. No. 14/869,762, dated Oct. 6, 2016.
Final Office Action, U.S. Appl. No. 15/274,717 dated Aug. 18, 2017.
Final Rejection, U.S. Appl. No. 13/749,095, dated Dec. 24, 2015.
Final Rejection, U.S. Appl. No. 14/476,500, dated Feb. 1, 2016.
Indian Examination Report, 3927/KOLNP/2010, dated Nov. 17, 2017.
International Search Report and Written Opinion, PCT/US2014/030496, dated Aug. 6, 2014.
International Search Report and Written Opinion, PCT/US2016/034847, dated Dec. 8, 2016.
International Search Report and Written Opinion, PCT/US2017/049466, dated Dec. 11, 2017.
Japanese Office Action, JP2014-147908, dated Jun. 9, 2015.
Non-Final Office Action, U.S. Appl. No. 14/335,460, dated Aug. 30, 2016.
Non-Final Office Action, U.S. Appl. No. 13/731,697, dated Jan. 29, 2015.
Non-Final Office Action, U.S. Appl. No. 13/749,095, dated Jan. 27, 2015.
Non-Final Office Action, U.S. Appl. No. 11/656,323, dated Sep. 18, 2014.
Non-Final Office Action, U.S. Appl. No. 13/488,505, dated Jul. 17, 2014.
Non-Final Office Action, U.S. Appl. No. 11/946,002, dated May 18, 2016.
Non-Final Office Action, U.S. Appl. No. 11/946,002, dated Jun. 29, 2015.
Non-Final Office Action, U.S. Appl. No. 13/749,095, dated Sep. 10, 2015.
Non-Final Office Action, U.S. Appl. No. 13/923,093, dated Dec. 2, 2015.
Non-Final Office Action, U.S. Appl. No. 13/960,498, dated Feb. 9, 2016.
Non-Final Office Action, U.S. Appl. No. 14/011,998, dated Feb. 12, 2016.
Non-Final Office Action, U.S. Appl. No. 14/084,255, dated Jan. 19, 2017.
Non-Final Office Action, U.S. Appl. No. 14/084,255, dated Feb. 25, 2016.
Non-Final Office Action, U.S. Appl. No. 14/086,849, dated Nov. 2, 2016.
Non-Final Office Action, U.S. Appl. No. 14/086,878, dated Nov. 10, 2016.
Non-Final Office Action, U.S. Appl. No. 14/272,147, dated Jun. 17, 2016.
Non-Final Office Action, U.S. Appl. No. 14/335,431, dated Sep. 14, 2016.
Non-Final Office Action, U.S. Appl. No. 14/476,500, dated Jun. 18, 2015.
Non-Final Office Action, U.S. Appl. No. 14/869,762, dated Mar. 31, 2016.
Non-Final Office Action, U.S. Appl. No. 14/869,762, dated Sep. 11, 2017.
Non-Final Office Action, U.S. Appl. No. 14/928,767, dated Jan. 12, 2017.
Non-Final Office Action, U.S. Appl. No. 14/928,767, dated Nov. 9, 2017.
Non-Final Office Action, U.S. Appl. No. 15/167,710, dated Nov. 3, 2017.
Non-Final Office Action, U.S. Appl. No. 15/168,359, dated Dec. 30, 2016.
Non-Final Office Action, U.S. Appl. No. 15/168,359, dated Aug. 17, 2016.
Non-Final Office Action, U.S. Appl. No. 15/168,405, dated Jan. 12, 2017.
Non-Final Office Action, U.S. Appl. No. 15/168,405, dated Aug. 3, 2016.
Non-Final Office Action, U.S. Appl. No. 15/274,717, dated Apr. 26, 2017.
Non-Final Office Action, U.S. Appl. No. 15/483,560, dated Sep. 28, 2017.
Non-Final Office Action, U.S. Appl. No. 15/581,974, dated Aug. 3, 2017.
Non-Final Office Action, U.S. Appl. No. 15/701,180, dated Nov. 9, 2017.
Notice of Allowance, U.S. Appl. No. 11/656,323, dated Feb. 3, 2015.
Notice of Allowance, U.S. Appl. No. 12/505,056, dated Mar. 6, 2014, 10 pages.
Notice of Allowance, U.S. Appl. No. 13/723,904, dated Mar. 7, 2014, 8 pages.
Notice of Allowance, U.S. Appl. No. 13/730,585, dated Mar. 18, 2014, 10 pages.
Notice of Allowance, 13/730,608, dated Apr. 18, 2014.
Notice of Allowance, U.S. Appl. No. 12/391,008, dated Dec. 22, 2015.
Notice of Allowance, U.S. Appl. No. 13/731,697, dated Jul. 29, 2015.
Notice of Allowance, U.S. Appl. No. 13/749,095, dated Apr. 7, 2016.
Notice of Allowance, U.S. Appl. No. 13/923,093, dated Jan. 4, 2017.
Notice of Allowance, U.S. Appl. No. 14/011,998, dated Jan. 11, 2017.
Notice of Allowance, U.S. Appl. No. 14/084,255, dated Jun. 8, 2017.
Notice of Allowance, U.S. Appl. No. 14/086,849, dated Jun. 6, 2017.
Notice of Allowance, U.S. Appl. No. 14/086,878, dated Jun. 14, 2017.
Notice of Allowance, U.S. Appl. No. 14/272,147, dated Nov. 21, 2016.
Notice of Allowance, U.S. Appl. No. 14/335,431, dated May 10, 2017.
Notice of Allowance, U.S. Appl. No. 14/335,460, dated Mar. 27, 2017.
Notice of Allowance, U.S. Appl. No. 14/476,500, dated May 19, 2016.
Notice of Allowance, U.S. Appl. No. 14/824,731, dated Oct. 20, 2015.
Notice of Allowance, U.S. Appl. No. 15/167,614, dated Aug. 26, 2016.
Notice of Allowance, U.S. Appl. No. 15/168,359, dated Jul. 14, 2017.
Notice of Allowance, U.S. Appl. No. 15/168,405, dated Jun. 7, 2017.
Notice of Allowance, U.S. Appl. No. 15/202,417, dated Oct. 12, 2017.
Notice of Allowance, U.S. Appl. No. 15/242,312, dated Jan. 3, 2017.
Notice of Allowance, U.S. Appl. No. 15/469,171, dated Aug. 7, 2017.
Preliminary Amendment, U.S. Appl. No. 13/731,850, filed Apr. 11, 2014, 8 pages.
Preliminary Amendment, U.S. Appl. No. 15/202,417, dated Sep. 15, 2016.
Response to Final Office Action, U.S. Appl. No. 12/505,056, dated Feb. 26, 2014, 19 pages.
Response to Final Office Action, U.S. Appl. No. 13/723,904, dated Feb. 19, 2014.

(56) References Cited

OTHER PUBLICATIONS

Response to Final Office Action, U.S. Appl. No. 13/730,585, dated Feb. 26, 2014, 9 pages.
Response to Final Office Action, U.S. Appl. No. 11/946,002, dated Mar. 29, 2016.
Response to Final Office Action, U.S. Appl. No. 13/749,095, dated Feb. 17, 2016.
Response to Final Office Action, U.S. Appl. No. 14/084,255, dated Dec. 22, 2016.
Response to Final Office Action, U.S. Appl. No. 14/869,762, dated Jan. 4, 2017.
Response to Final Office Action, U.S. Appl. No. 15/274,717, dated Nov. 13, 2017.
Response to Non-Final Office Action, U.S. Appl. No. 13/731,697, dated May 26, 2015.
Response to Non-Final Office Action, U.S. Appl. No. 13/749,095, dated Apr. 20, 2015.
Response to Non-Final Office Action, U.S. Appl. No. 13/730,467, dated Apr. 11, 2014, 8 pages.
Response to Non-Final Office Action, U.S. Appl. No. 11/946,002, dated Sep. 29, 2015.
Response to Non-Final Office Action, U.S. Appl. No. 13/923,093, dated May 2, 2016.
Response to Non-Final Office Action, U.S. Appl. No. 14/011,998, dated May 6, 2016.
Response to Non-Final Office Action, U.S. Appl. No. 14/084,255, dated Apr. 19, 2017.
Response to Non-Final Office Action, U.S. Appl. No. 14/084,255, dated May 23, 2016.
Response to Non-Final Office Action, U.S. Appl. No. 14/086,849, dated Apr. 3, 2017.
Response to Non-Final Office Action, U.S. Appl. No. 14/086,878, dated Apr. 4, 2017.
Response to Non-Final Office Action, U.S. Appl. No. 14/272,147, dated Sep. 13, 2016.
Response to Non-Final Office Action, U.S. Appl. No. 14/335,460, dated Jan. 27, 2017.
Response to Non-Final Office Action, U.S. Appl. No. 14/476,500, dated Oct. 16, 2015.
Response to Non-Final Office Action, U.S. Appl. No. 14/869,762, dated Jun. 29, 2016.
Response to Non-Final Office Action, U.S. Appl. No. 14/928,767, dated Apr. 12, 2017.
Response to Non-Final Office Action, U.S. Appl. No. 15/168,359, dated Oct. 24, 2016.
Response to Non-Final Office Action, U.S. Appl. No. 15/168,359, dated Mar. 30, 2017.
Response to Non-Final Office Action, U.S. Appl. No. 15/168,405 dated Oct. 31, 2016.
Response to Non-Final Office Action, U.S. Appl. No. 15/168,405, dated Apr. 7, 2017.
Response to Non-Final Office Action, U.S. Appl. No. 15/274,717, dated Jul. 17, 2017.
Response to Restriction, U.S. Appl. No. 14/476,500, dated Mar. 17, 2015.
Response to Restriction, U.S. Appl. No. 13/749,095, dated Nov. 13, 2014.
Response to Restriction, U.S. Appl. No. 13/960,498, dated Nov. 19, 2015.
Response to Restriction, U.S. Appl. No. 14/335,431, dated Aug. 31, 2016.
Response to Restriction, U.S. Appl. No. 14/928,767, dated Aug. 22, 2017.
Response to Restriction, U.S. Appl. No. 15/274,717, dated Jan. 9, 2017.
Restriction Requirement, U.S. Appl. No. 14/476,500, dated Feb. 25, 2015.
Restriction Requirement, U.S. Appl. No. 13/488,505, dated Mar. 4, 2014, 5 pages.
Restriction Requirement, U.S. Appl. No. 13/749,095, dated Sep. 25, 2014.
Restriction Requirement, U.S. Appl. No. 13/960,498, dated Sep. 23, 2015.
Restriction Requirement, U.S. Appl. No. 14/335,431, dated Aug. 12, 2016.
Restriction Requirement, U.S. Appl. No. 14/928,767, dated Jul. 28, 2017.
Restriction Requirement, U.S. Appl. No. 15/274,717, dated Nov. 16, 2016.
Supplemental Amendment, U.S. Appl. No. 14/869,762, dated Jan. 13, 2017.
Supplementary European Search Report and Opinion, EP 09739474.6, dated Feb. 27, 2014, 7 pages.

* cited by examiner

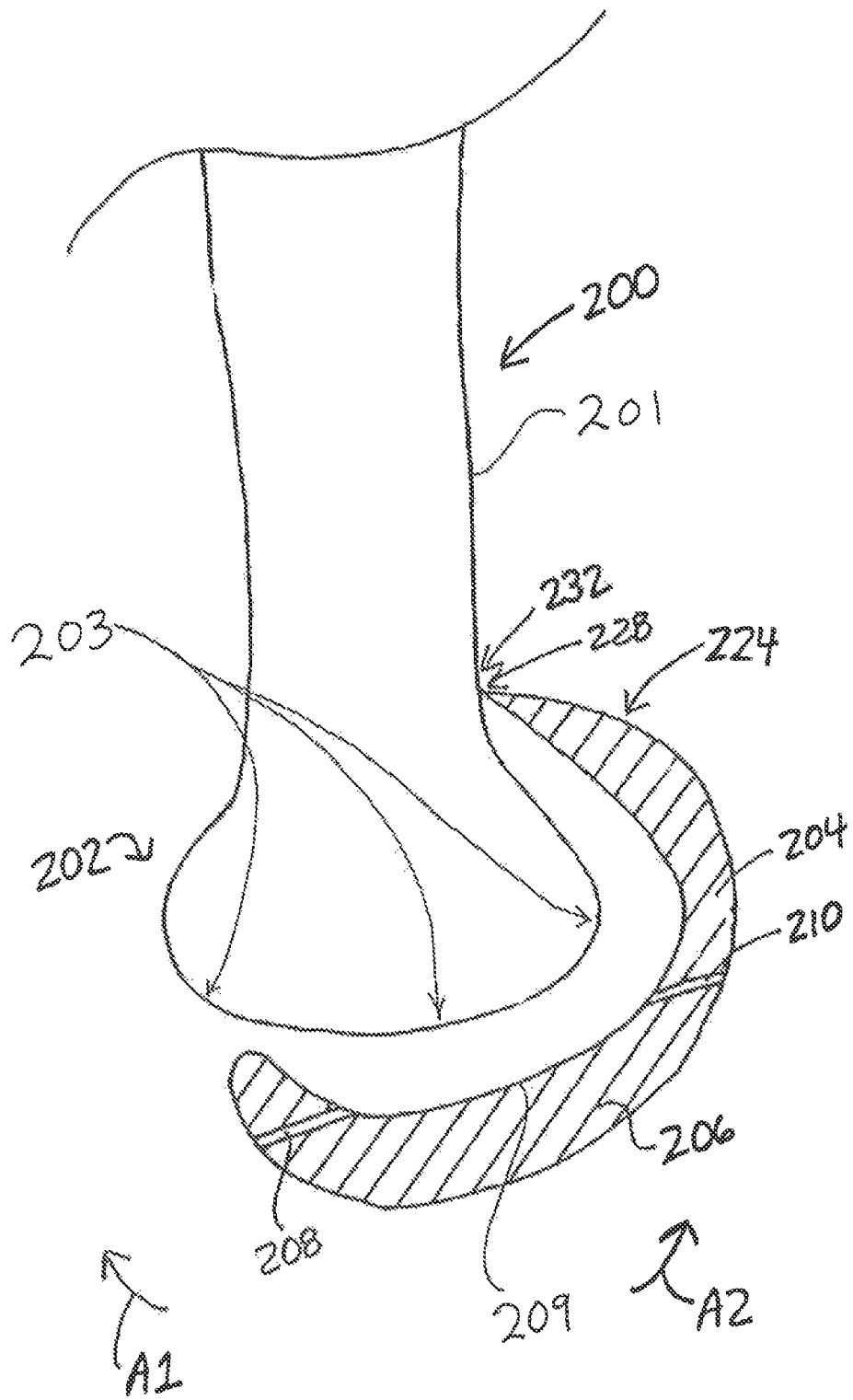

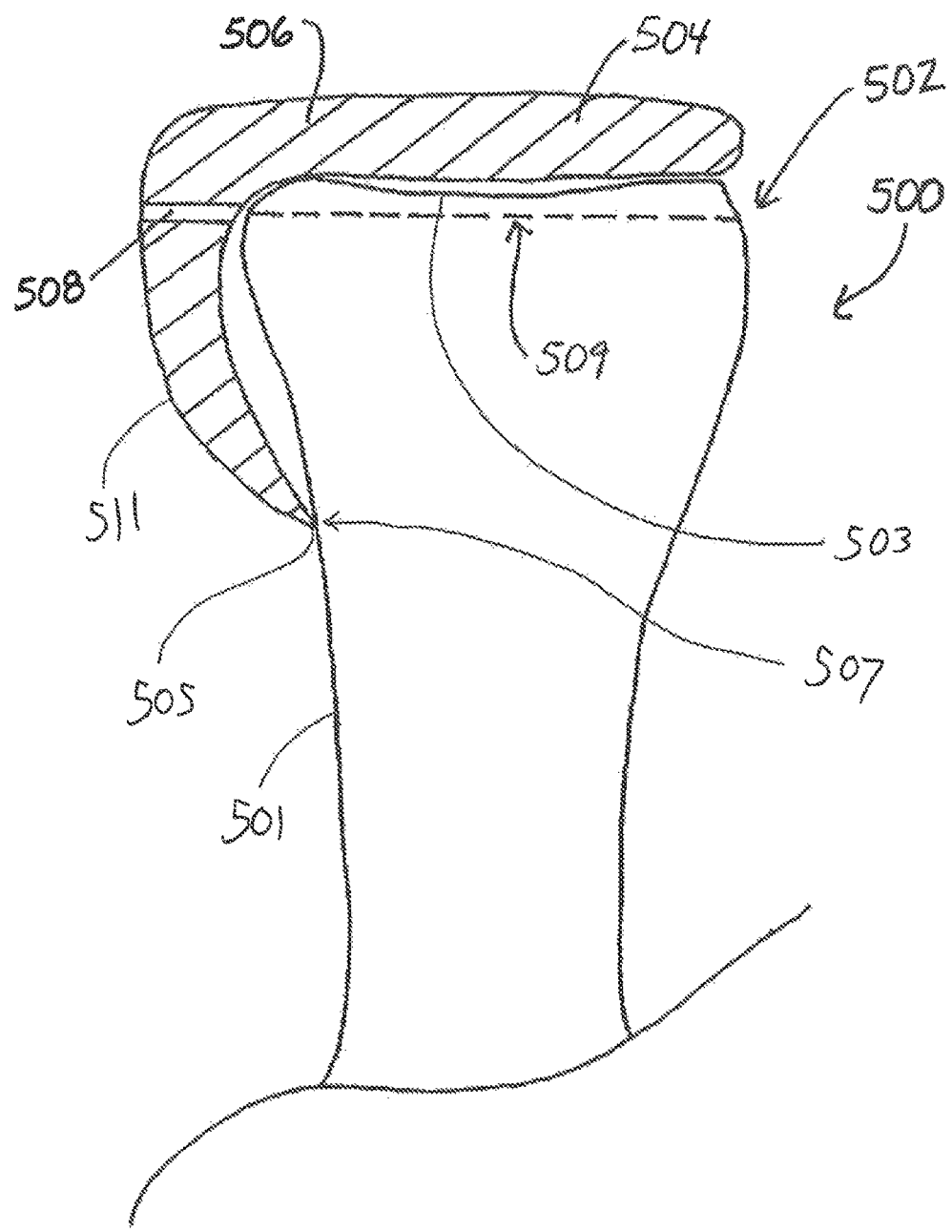

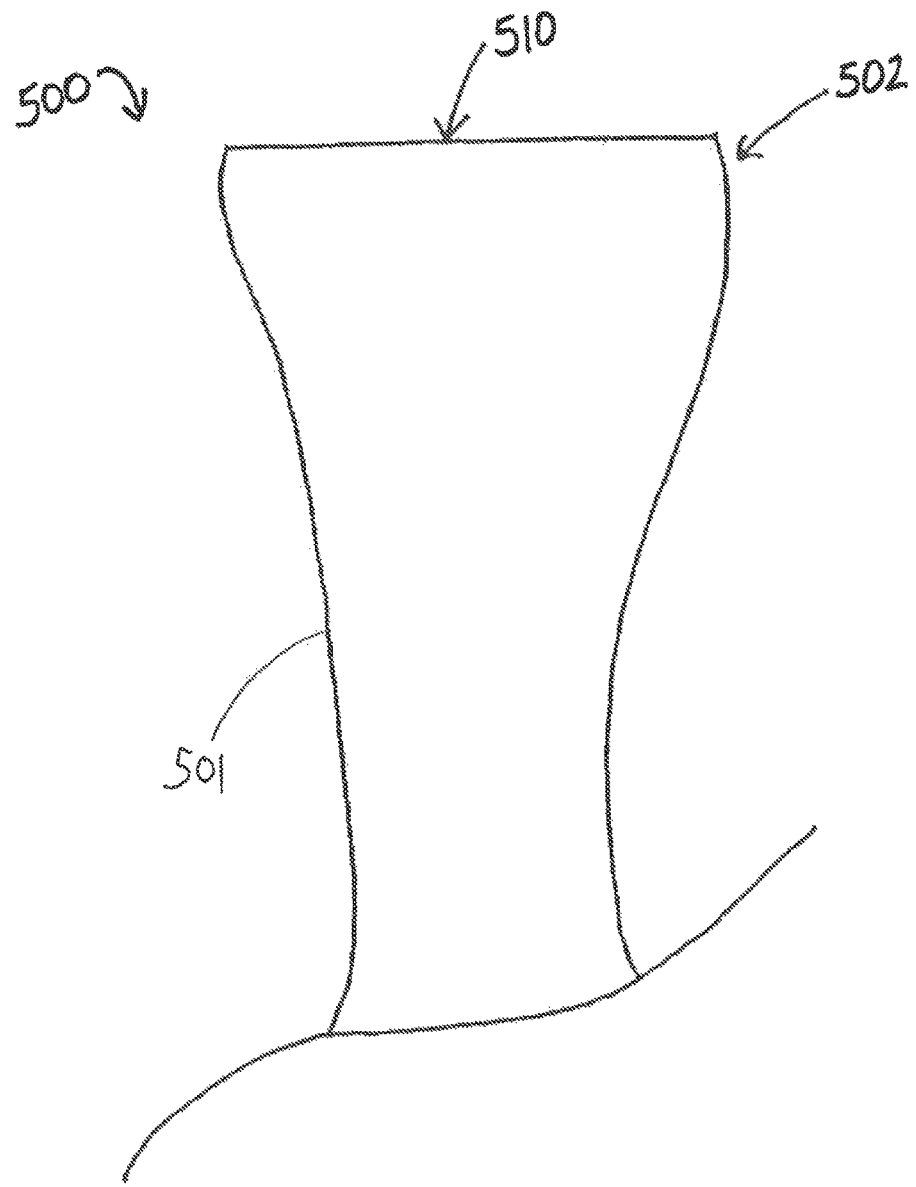

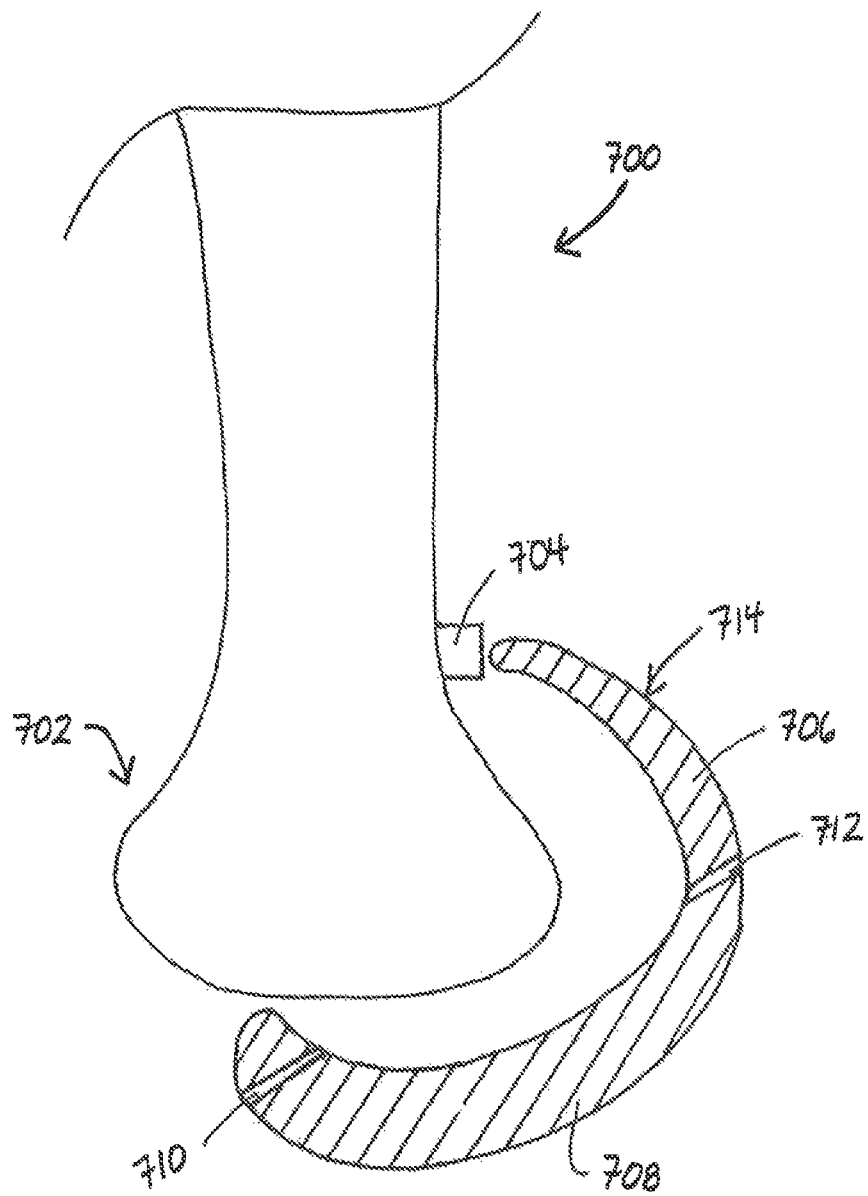

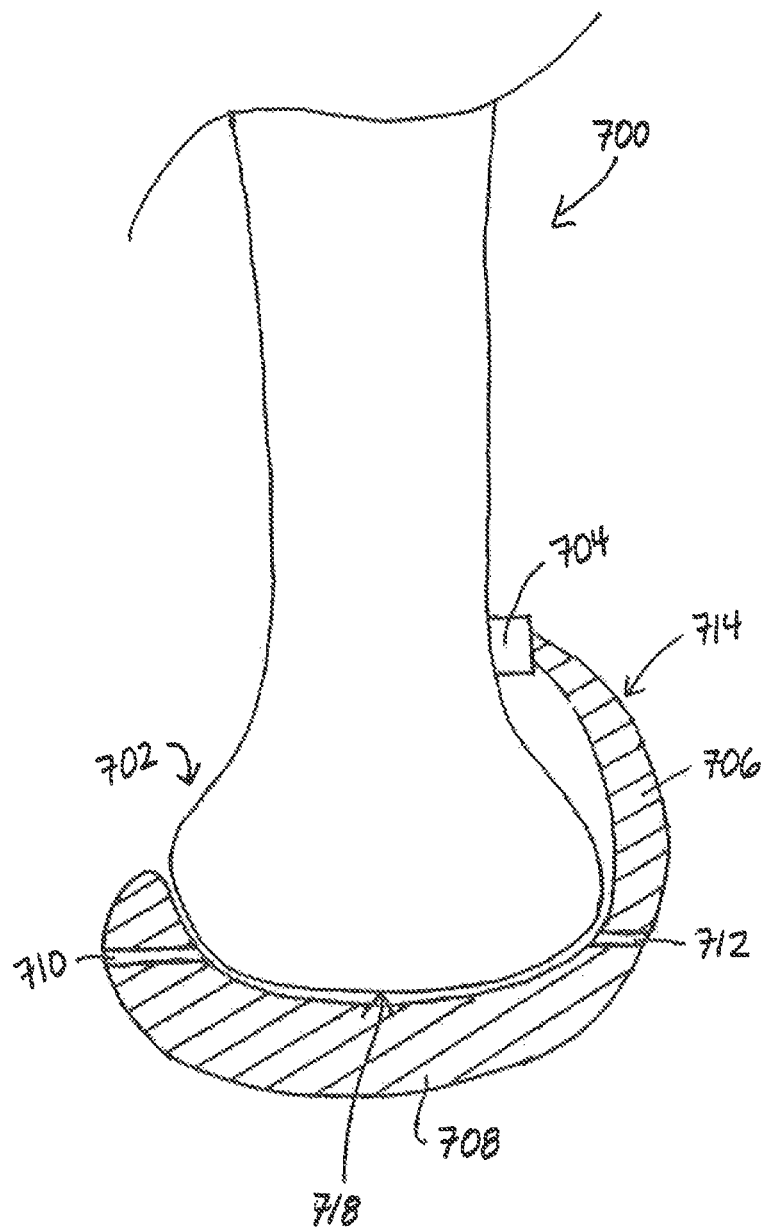

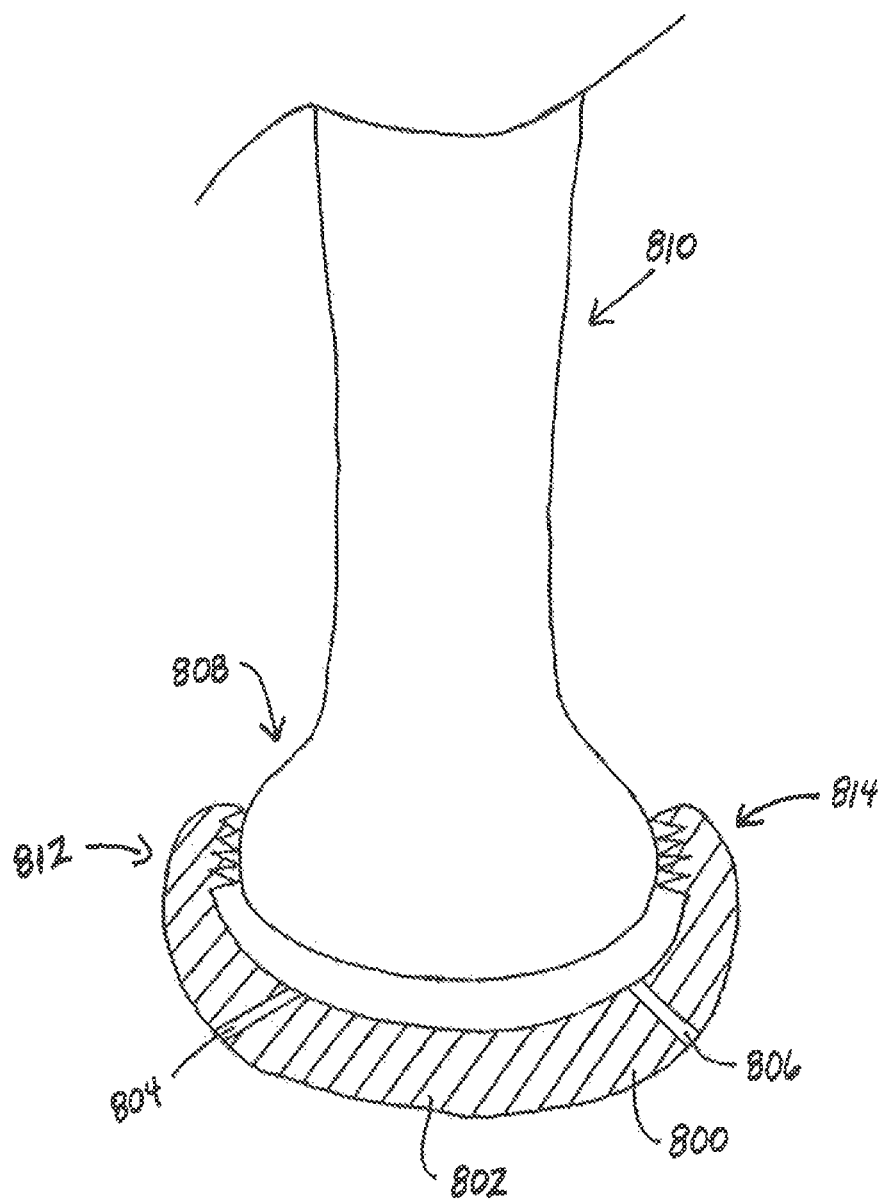

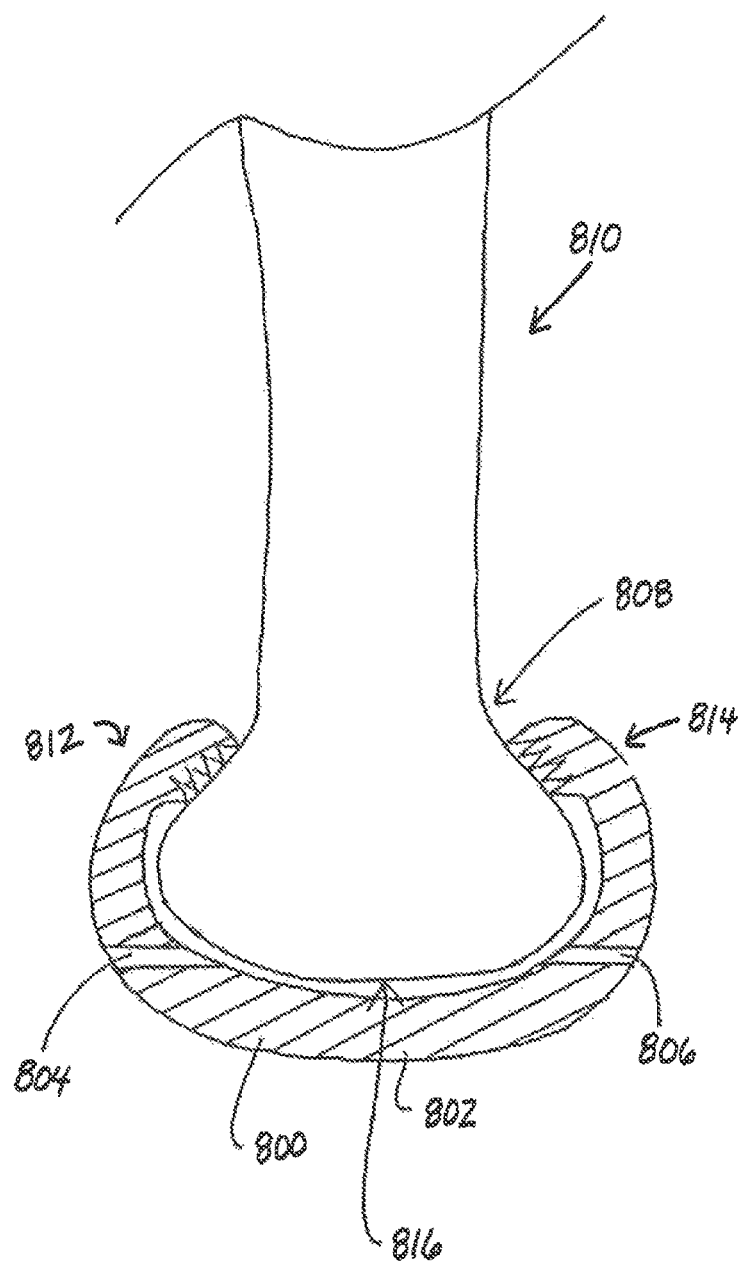

ARTHROPLASTY DEVICES AND RELATED METHODS

CROSS-REFERENCE TO RELATED APPLICATIONS

This application is a continuation of U.S. application Ser. No. 11/642,385 filed Dec. 19, 2006, which application claims the benefit of priority under 35 U.S.C. § 119(e), to U.S. Provisional Patent Application No. 60/773,491, filed on Feb. 15, 2006. The above-referenced applications are incorporated by reference in their entireties for all that they disclose or teach.

TECHNICAL FIELD

The methods and devices described herein relate generally to the field of implants, as well as jigs that may be used to position and align implants at a target site; More specifically, the methods and devices described herein relate to the field of selecting an arthroplasty jig that corresponds to a specific target site, and accurately positioning and aligning the arthroplasty jig at the target site.

BACKGROUND

Over time and through repeated use, bones and joints can become damaged or worn. For example, repetitive strain on bones and joints (e.g., through athletic activity), traumatic events, and certain diseases (e.g., arthritis) can cause cartilage in joint areas to wear down. As a result, fluid can accumulate in these joint areas, resulting in pain, stiffness, and decreased mobility.

Arthroplasty procedures can be used to repair damaged joints. During a typical arthroplasty procedure, an arthritic or otherwise dysfunctional joint can be remodeled or realigned, or an implant can be implanted into the damaged region. Arthroplasty procedures may take place in any of a number of different regions of the body, such as a knee, a hip, a shoulder, or an elbow.

As mentioned above, during some arthroplasty procedures, an implant may be implanted into the damaged region. The implant may provide support and structure to the damaged region, and may help to restore the damaged region, thereby enhancing its functionality. Prior to implantation of the implant in the damaged region, the damaged region can be prepared to receive the implant. For example, in a knee arthroplasty procedure, one or more of the bones in the knee area, such as the femur and/or tibia, may be treated (e.g., cut, drilled, reamed, and/or resurfaced) to provide one or more surfaces that can align with the implant and thereby accommodate the implant.

Prior to treating any regions of a bone, it is important to correctly determine the location at which the treatment will take place. In some methods, an arthroplasty jig may be used to accurately position an instrument, such as a cutting, drilling, reaming, or resurfacing instrument, at a target site. The instrument can, in turn, be used to prepare the target site for an implant prior to delivery of the implant to the target site. The arthroplasty jig may, for example, include one or more apertures and/or slots that are configured to accept the instrument.

In order for an arthroplasty jig to accurately position an instrument at a target site, however, the arthroplasty jig itself should be accurately positioned and aligned at the target site. Accordingly, it would be desirable to provide methods and devices that allow for identification and selection of the correct arthroplasty jig for use at a particular target site, as well as methods and devices that allow for the precise positioning and alignment of an arthroplasty jig at a target site.

BRIEF SUMMARY

Described here are methods and devices that may be used to help identify a suitable arthroplasty jig for use at a target site, as well as methods and devices that may be used to enhance the positioning and alignment of an arthroplasty jig at a target site. The methods and devices described here include certain features that may enhance the customization of an arthroplasty procedure, and may thereby result in reduced procedure time and recovery time, as well as a reduced likelihood of complications.

Some of the arthroplasty jigs described here comprise a jig body that is configured to align with a surface of a bone, and a positioning component that is configured to provide at least one of a visible, audible, or tactile indication when the jig body has aligned with the surface of the bone. Similarly, some of the methods described here comprise providing an arthroplasty jig comprising a jig body and a positioning component, and aligning the jig body with a surface of a bone so that the positioning component provides at least one of a visible, audible, or tactile indication that such alignment has been achieved. The methods may further comprise cutting, drilling, reaming, and/or resurfacing the bone. The presence of the positioning component as part of the arthroplasty jig may increase the likelihood that this cutting, drilling, reaming, and/or resurfacing occurs in the right location.

Certain of the arthroplasty jigs described here comprise a jig body that is marked with identifying information, and that is configured to align with a surface of a bone. Similarly, certain of the arthroplasty jig blanks described here (which are used to form arthroplasty jigs) are marked with identifying information. Some of the methods described here comprise providing an arthroplasty jig blank, or an arthroplasty jig comprising a jig body that is configured to align with a surface of a bone, and marking the arthroplasty jig blank or the jig body with identifying information. The markings on an arthroplasty jig blank may decrease the likelihood of the wrong arthroplasty jig blank being selected to form a particular arthroplasty jig. An arthroplasty jig that is formed from an arthroplasty jig blank may retain some or all of the markings that originally were on the arthroplasty jig blank, and thus may be readily identifiable. The markings on a marked arthroplasty jig may be used, for example, to assist in positioning and aligning the arthroplasty jig at a target site, and/or to readily identify the arthroplasty jig prior to or during an arthroplasty procedure.

Arthroplasty jigs, arthroplasty jig blanks, and related methods may include just one of the features described herein, or more than one of the features described herein. For example, in some variations, an arthroplasty jig may include both a positioning component and one or more markings that provide identifying information about the arthroplasty jig.

The positioning component may be attached to the jig body, or may be integrally formed with the jig body. In some variations, the positioning component may comprise a rod. In such variations, the jig body may comprise an aperture, and the positioning component may at least partially extend through the aperture. In certain variations, the positioning component may comprise a projection extending from the jig body. In some variations, the positioning component may be hook-shaped.

In certain variations in which the jig body is marked with identifying information, the identifying information may be engraved into the jig body, printed onto the jig body, and/or provided on a label that is affixed to the jig body. Examples of engraving methods include carving, cutting, and etching (e.g., laser etching). The identifying information may include, for example, patient data, doctor information, information regarding the size and/or materials of the jig body, company logos, barcodes, etc.

The arthroplasty jig may be configured for use in at least one of cutting, drilling, reaming, or resurfacing a bone during an arthroplasty procedure. For example, the jig body may comprise at least one slot or aperture that is configured to accept an instrument, such as a cutting instrument (e.g., a reciprocating saw blade). The jig body may be configured so that the cutting instrument can be used in conjunction with the arthroplasty jig to remove a portion of a bone to provide a substantially planar surface on the bone. The substantially planar surface, in turn, may be configured to align with a surface of an implant device. Examples of bones with which the arthroplasty jigs and methods may be used include femurs and tibias.

BRIEF DESCRIPTION OF THE DRAWINGS

FIG. 2D is an illustration of the portion of the femur of FIG. 2A, when the arthroplasty jig of FIG. 2A is not aligned with the portion of the femur.

FIG. 5A is an illustration of a portion of a tibia of a subject, and an arthroplasty jig aligned with the portion of the tibia.

FIG. 5B is an illustration of the portion of the tibia of FIG. 5A, after the portion has been cut using a cutting instrument.

FIG. 7A is an illustration of an arthroplasty jig as the arthroplasty jig is being positioned on a portion of a femur of a subject.

FIG. 7B is an illustration of the arthroplasty jig of FIG. 7A, after it has been aligned with the portion of the femur of FIG. 7A.

FIG. 8A is an illustration of an arthroplasty jig as the arthroplasty jig is being positioned on a portion of a femur of a subject.

FIG. 8B is an illustration of the arthroplasty jig of FIG. 8A, after it has been aligned with the portion of the femur of FIG. 8A.

DETAILED DESCRIPTION

Described here are arthroplasty jigs, and methods of making and using arthroplasty jigs, having features that may provide for enhanced alignment and positioning of the arthroplasty jigs at a target site. This enhanced arthroplasty jig alignment and positioning may, in turn, result in enhanced implant alignment and positioning at the target site. As the implant alignment and positioning of an implant are improved, the result may be a decreased likelihood of follow-up surgery (e.g., to adjust the alignment of the implant), and/or an increase in the useful life of the implant. Additional results may include reduced procedure time and fewer complications during and/or after surgery. It should be understood from the outset that while knee arthroplasty jigs are described in detail here, one or more of the features or methods described here may be employed with other types of arthroplasty jigs, such as arthroplasty jigs that are suited for use in the hip, shoulder, elbow, etc.

Figure 1:
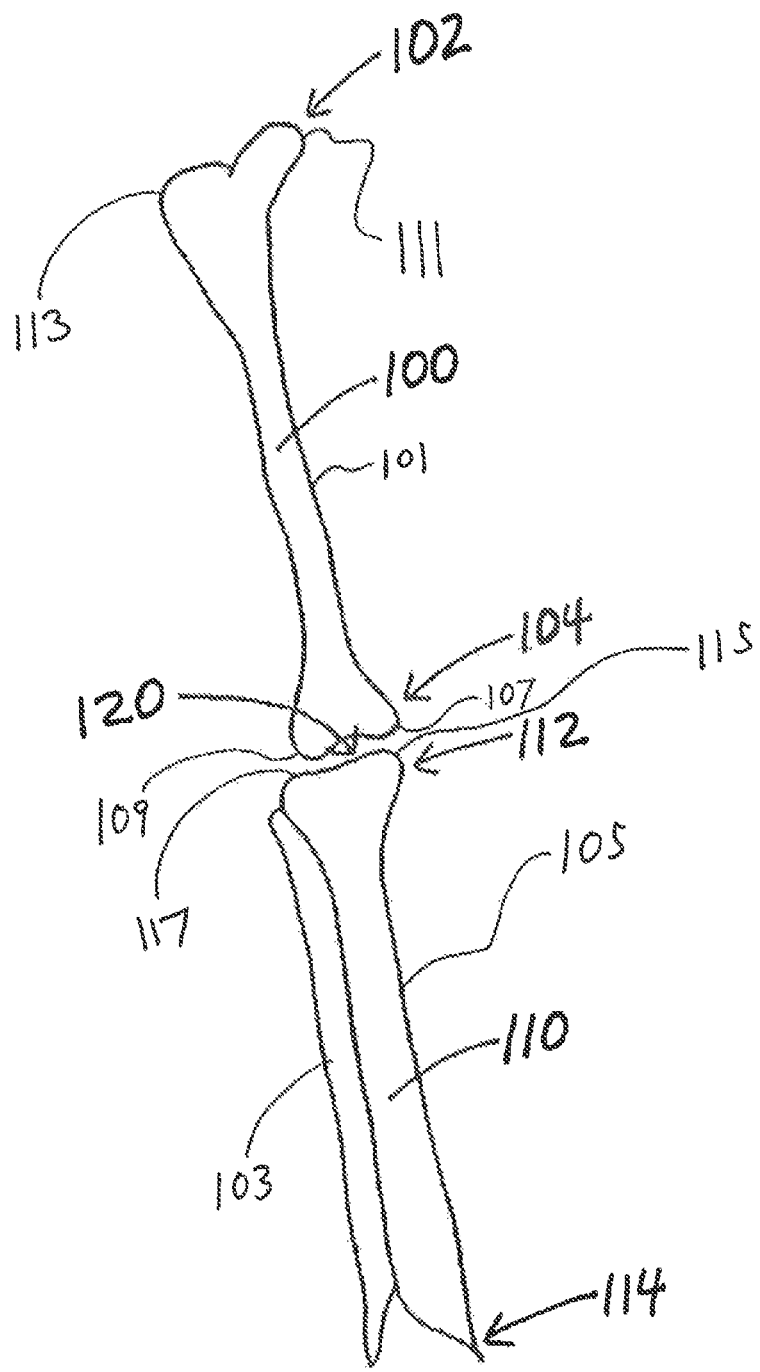
FIG. 1 is an illustration of leg bones of a subject.

Turning now to the figures, FIG. 1 is an illustration of the anterior sides of the leg bones of a human subject. As shown in FIG. 1, the leg bones include a femur (100) having a proximal end (102) and a distal end (104), a tibia (110) having a proximal end (112) and a distal end (114), and a fibula (103) extending generally parallel to the tibia (110). The femur (100) includes a shaft (101) that extends between the proximal end (102) and the distal end (104), and the tibia (110) includes a shaft (105) that extends between the proximal end (112) and the distal end (114). The femur distal end (104) includes a knee joint region that articulates with a corresponding knee joint region of the tibia proximal end (112) and includes a medial condyle (107) and a lateral condyle (109). The femur proximal end (102) combines with the pelvis to form the hip joint and includes a head (111) and a greater trochanter (113). The tibia proximal end (112) includes a knee joint region that articulates with the corresponding knee joint region of the femur distal end (104) and includes a medial plateau (115) and a lateral plateau (117). A joint (120) is formed between the femoral distal end (104)

and the tibial proximal end (112), and may, as a result of damage or wear, require repair or restoration using, for example, an arthroplasty procedure.

As discussed above, in some variations of an arthroplasty procedure, one or more arthroplasty jigs may be used to help prepare a damaged bone region for an implant. The arthroplasty jigs may be used, for example, to aid in the correct placement of certain instruments, such as cutting, drilling, reaming, and resurfacing instruments. As an example, some arthroplasty procedures may include using an arthroplasty jig to accurately position a reciprocating saw blade. The reciprocating saw blade may be used, for example, to cut the damaged bone region to provide one or more planar surfaces. The planar surfaces may assist in the alignment and positioning of an implant at a target site in the damaged bone region. Arthroplasty jigs may also be used, for example, to position one or more pins that secure an implant to a target site in the damaged bone region.

Figure 2A:
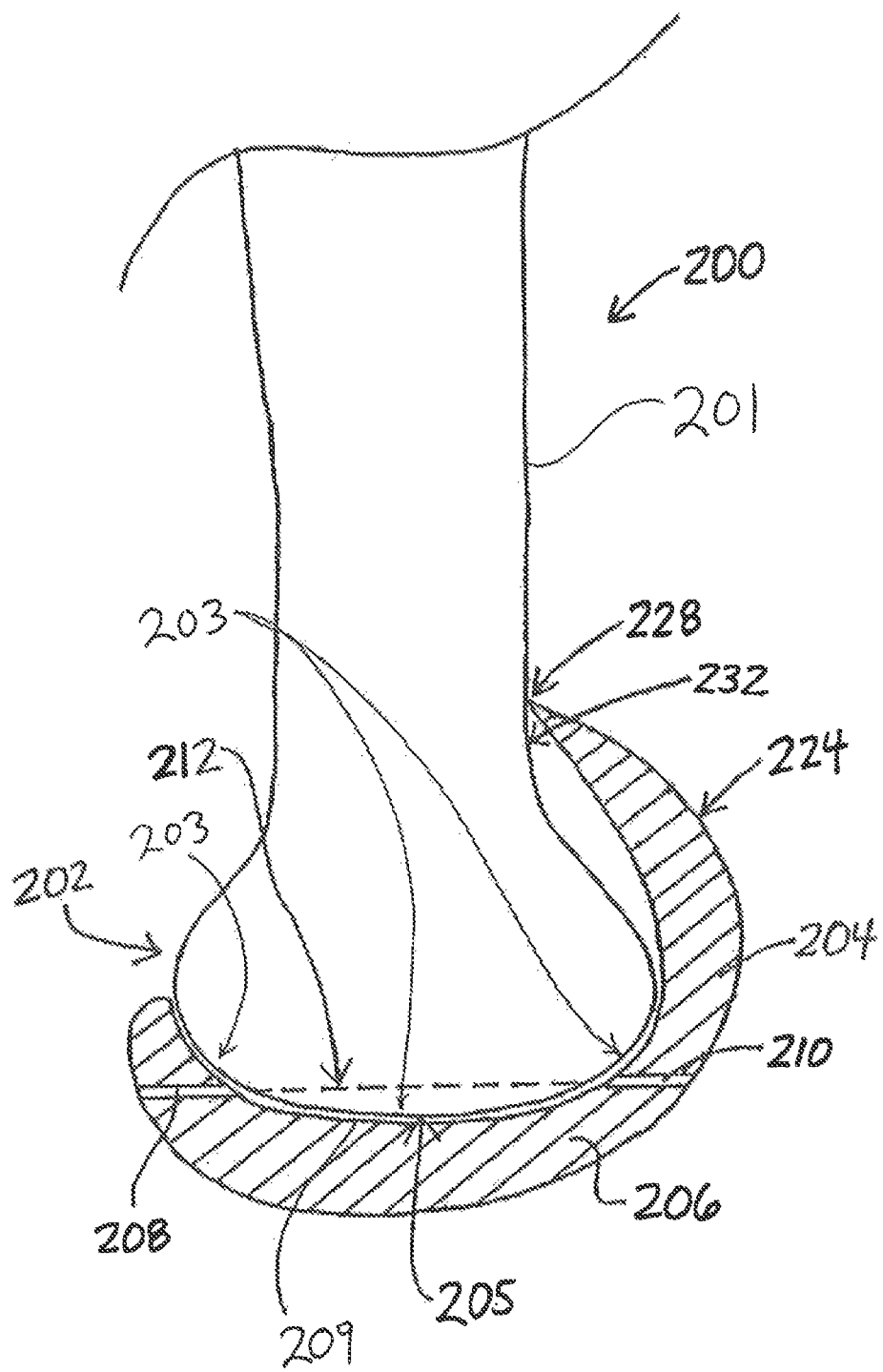
FIG. 2A is an illustration of a portion of a femur of a subject, and an arthroplasty jig aligned with the portion of the femur.
Figure 2B:
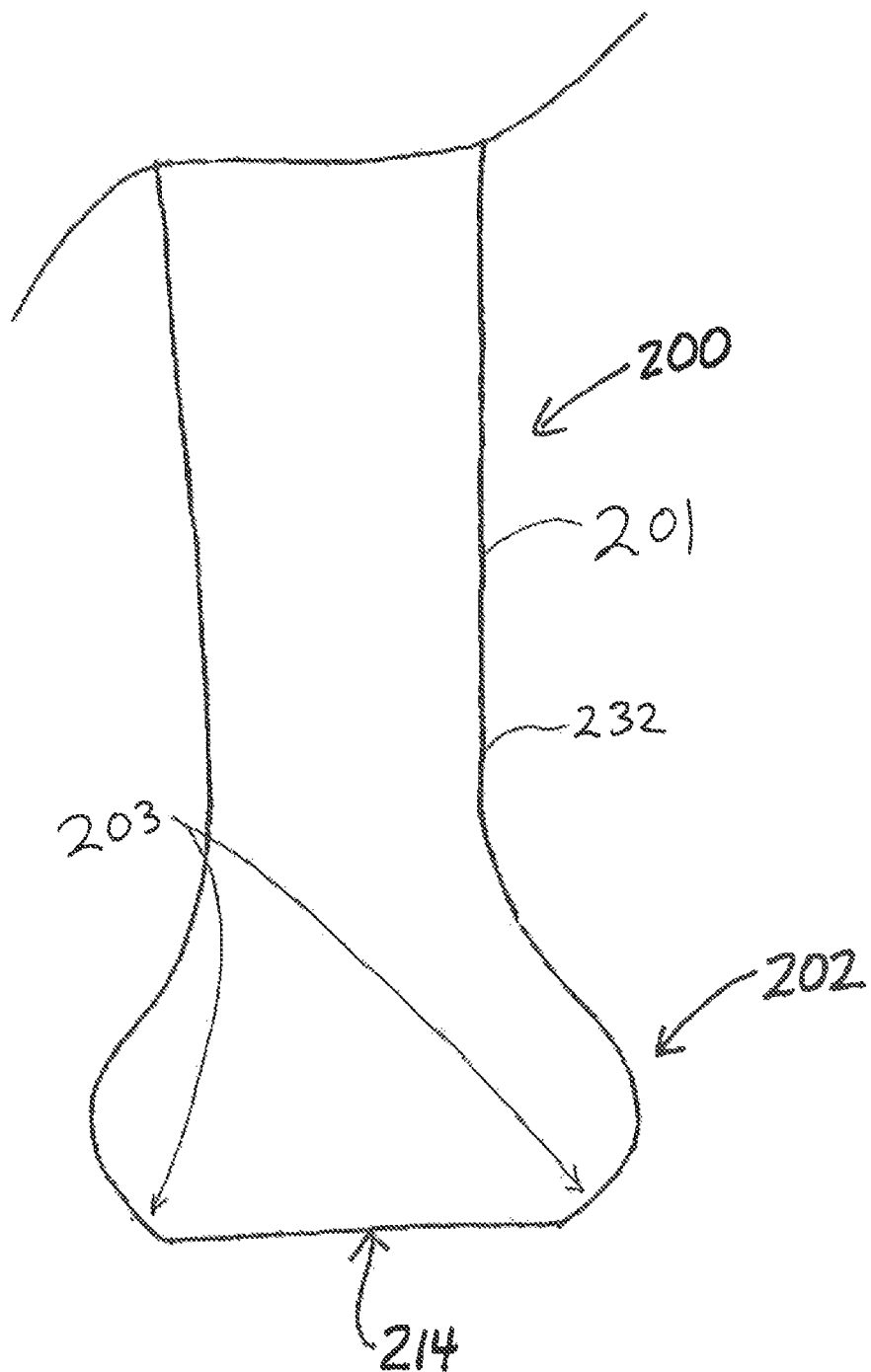
FIG. 2B is an illustration of the portion of the femur of FIG. 2A, after the portion has been cut using a cutting instrument.

A femoral arthroplasty jig is shown in FIG. 2A. As shown in FIG. 2A, a femur (200) has a femoral distal end (202) distally extending from the femoral shaft (201) and including a condyle region (203). An arthroplasty jig (204) includes a surface (209) that is aligned with a surface (205) of condyle region (203), and has a jig body (206) including two slots (208) and (210). Slots (208) and (210) can be used, for example, to position a cutting instrument (e.g., a reciprocating saw blade). The cutting instrument, in turn, can be used to form a cut (212) that removes a portion of distal end (202) of femur (200). The result, as shown in FIG. 2B, is a planar surface (214) along distal end (202) of femur (200). Planar surface (214) may, for example, align with a corresponding planar surface of an implant that is implanted into a damaged region of the knee that is at least partially defined by femur (200).

Referring back to FIG. 2A, arthroplasty jig (204) includes a positioning component (as shown, a projection (224)) that is integrally formed with jig body (206). Projection (224) has a pointed end (228). FIG. 2A shows arthroplasty jig (204) when it has been properly aligned with surface (205) of distal end (202) of femur (200), as indicated by projection (224) contacting a surface (232) of femur (200), for example, the femoral shaft surface (232). As a physician is positioning arthroplasty jig (204) on femur (200), the contact between pointed end (228) and femoral shaft surface (232) can provide the physician with a tactile indication that the arthroplasty jig has been properly positioned and aligned on femur (200). In other words, the physician may sense the contact between the pointed end and the surface of the femoral shaft. This contact may feel different to the physician, relative to the contact between other portions of arthroplasty jig (204) and femur (200). For example, at the other contact points, the arthroplasty jig may actually be contacting cartilage, whereas pointed end (228) contacts bone when arthroplasty jig (204) is properly positioned and aligned. Contact between an arthroplasty jig and cartilage typically feels different from contact between an arthroplasty jig and bone. Upon sensing the contact between pointed end (228) and shaft surface (232) of femur (200), the physician knows that the desired alignment has been achieved, and that the arthroplasty jig can stop being adjusted.

Figure 2C:
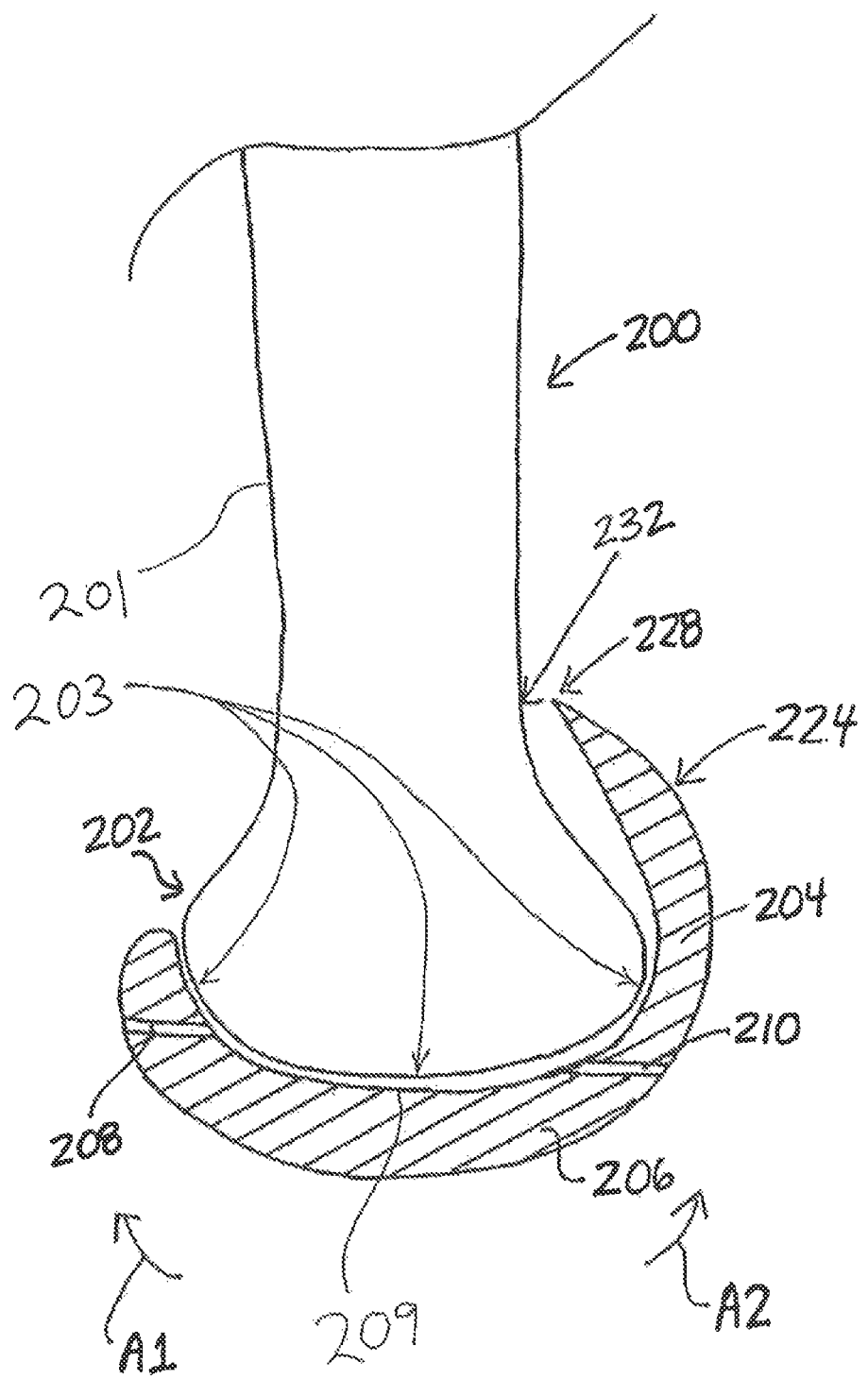
FIG. 2C is an illustration of the portion of the femur of FIG. 2A, when the arthroplasty jig of FIG. 2A is not aligned with the portion of the femur.

FIGS. 2C and 2D show arthroplasty jig (204) when it has not been properly positioned and aligned on femur (200). In FIG. 2C, arthroplasty jig (204) is positioned too far in the direction of arrow (A1), and not far enough in the direction of arrow (A2). Accordingly, and as shown in FIG. 2C, pointed end (228) of projection (224) does not contact shaft surface (232) of femur (200). FIG. 2D, on the other hand, shows arthroplasty jig (204) when it has been moved too far in the direction of arrow (A2). This may occur, for example, if the physician does not stop adjusting the arthroplasty jig after pointed end (228) has contacted shaft surface (232), and instead continues to move the arthroplasty jig in the direction of arrow (A2). The result is that jig body (206) pivots about the point of contact between pointed end (228) and shaft surface (232). This pivoting sensation notifies the physician that the position of the arthroplasty jig should be adjusted back in the direction of arrow (A1), rather than arrow (A2).

Figure 3A:
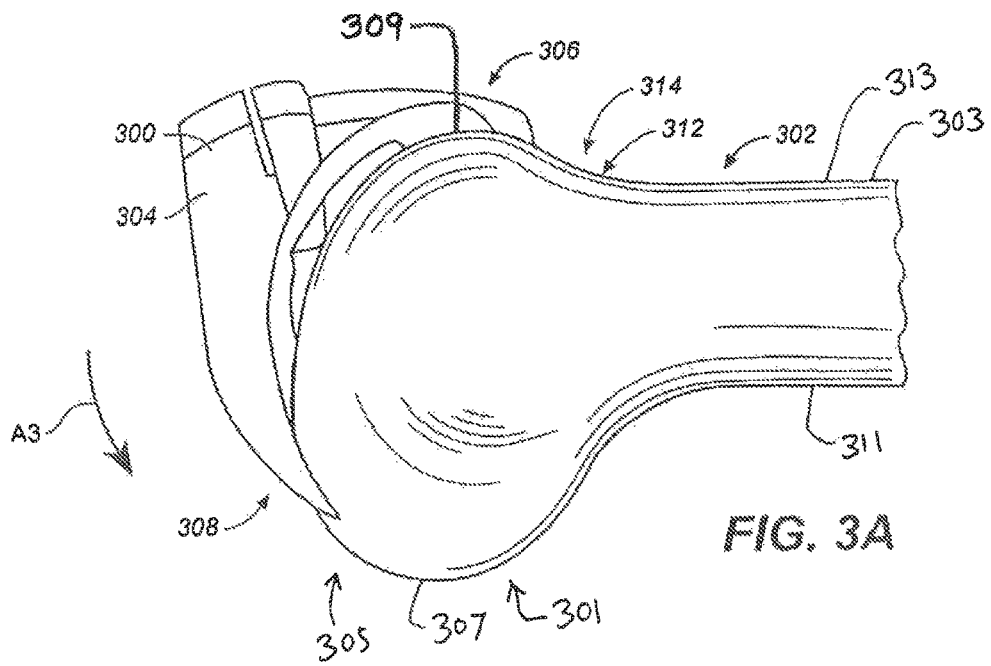
FIG. 3A is an illustration of a portion of a femur of a subject, and an arthroplasty jig being positioned on the portion of the femur.
Figure 3B:
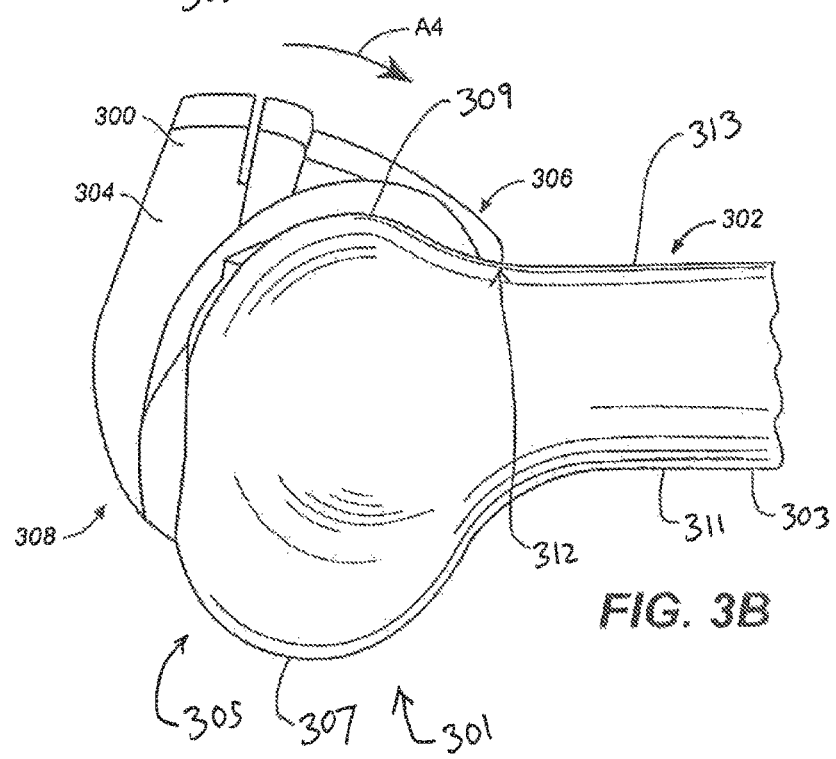
FIG. 3B is an illustration of the portion of the femur of FIG. 3A, and the arthroplasty jig of FIG. 3A being positioned on the portion of the femur.

FIGS. 3A and 3B show another variation of an arthroplasty jig (300) on a femoral distal end (301) extending from a femoral shaft (303). The femoral distal end (301) includes a condyle region (305) with a posterior side (307) and an anterior side (309), and the femoral shaft (303) includes a posterior side (311) and anterior side (313). In FIG. 3A, arthroplasty jig (300) is being positioned on a distal portion of a femur (302). Arthroplasty jig (300) includes a jig body (304) and projections (306) and (308) that extend from opposite ends of jig body (304) and that are integrally formed with jig body (304). When arthroplasty jig (300) is properly positioned on femur (302), projection (306) contacts an inflection point (312) on femur (302). For example, projection (306) contacts the anterior femoral shaft surface (312). However, and as FIG. 3A shows, if the physician adjusts arthroplasty jig (300) too far in the direction of arrow (A3), then projection (308) will become a pivoting point, and projection (306) will slide over a surface (314) of femur (302), away from inflection point (312). This misalignment of arthroplasty jig (300) may be visible to the physician. Furthermore, and referring now to FIG. 3B, if the physician tries to adjust arthroplasty jig (300) too far in the direction of arrow (A4), then projection (306) similarly becomes a pivoting point that indicates that arthroplasty jig (300) has not been properly positioned on femur (302).

Figure 4:
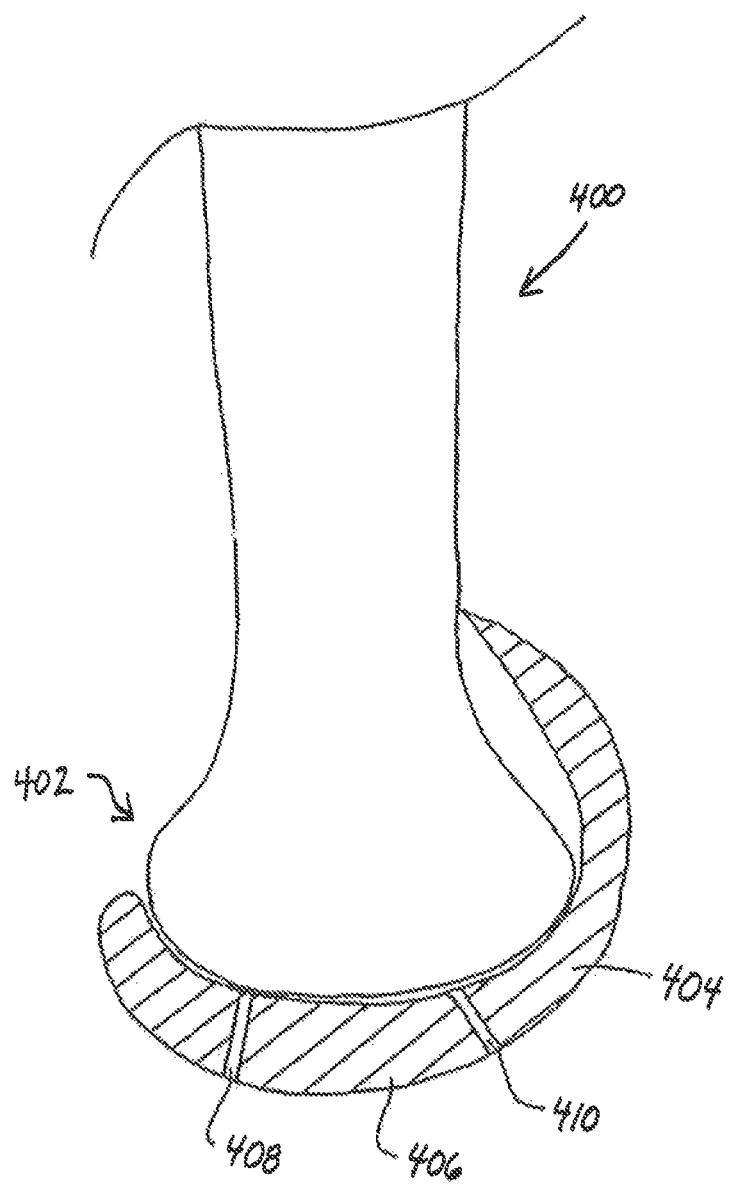
FIG. 4 is an illustration of a portion of a femur of a subject, and an arthroplasty jig aligned with the portion of the femur.

While the slots in some of the above arthroplasty jigs (such as slots (208) and (210) of arthroplasty jig (204)) have been described as being useful for positioning a cutting instrument, some variations of arthroplasty jigs may include one or more slots and/or apertures that are configured for other purposes. As an example, FIG. 4 shows a femur (400) having a distal end (402), as well as an arthroplasty jig (404) that is aligned with distal end (402). Arthroplasty jig (404) includes a jig body (406) having two apertures (408) and (410). Apertures (408) and (410) may be used, for example, to assist in the placement of one or more pins that help to secure an implant to femur (400).

While arthroplasty jigs having one or two slots or apertures have been shown, arthroplasty jigs can have any number of slots, apertures, grooves, and/or ridges. The number and type of features on an arthroplasty jig may be selected, for example, based on the proposed modifications to the target site. Arthroplasty jigs can also be configured for use in forming more than one planar surface in a damaged bone region. For example, an arthroplasty jig may be used to form two or three planar surfaces in a damaged bone region. The multiple planar surfaces may correspond to multiple planar surfaces in an implant that is to be inserted into the damaged bone region. Moreover, the slots, apertures, grooves, and/or ridges may be used for other purposes besides the aforementioned cutting, drilling, reaming, resurfacing, and pin positioning. For example, grooves and/or ridges on an arthroplasty jig may provide the arthroplasty jig with a surface morphology that helps the arthroplasty jig to be accurately positioned at a target site.

Arthroplasty jigs may be used in many other regions of the body besides a femur. For example, FIG. 5A shows a tibial arthroplasty jig. As shown in FIG. 5A, a tibia (500) has a proximal end (502) proximally extending from the tibia shaft (501) and including a plateau region (503). An arthroplasty jig (504) is aligned with proximal end (502), and has a body (506) including a slot (508). Slot (508) can be used to position a cutting instrument (e.g., a reciprocating saw blade) that, in turn, can be used to form a cut (509) in proximal end (502) of tibia (500). The result, as shown in FIG. 5B, is a planar surface (510) along proximal end (502) of tibia (500). Planar surface (510) may, for example, align with a corresponding planar surface of an implant that is implanted into a damaged region of the knee that is at least partially defined by tibia (500).

While the arthroplasty jigs shown above include positioning components in the form of projections (224), (511) having pointed ends (228), (505) that contact femoral and tibia bone surfaces, e.g., femoral shaft surfaces (232) and tibia shaft surfaces (507), arthroplasty jigs may include other types of positioning components. As an example, an arthroplasty jig may include a positioning component in the form of a projection having a rounded end. Positioning components may be integrally formed with, or attached to, the jig body of an arthroplasty jig. Examples of methods that may be used to attach a positioning component to a jig body include welding and bonding (e.g., adhesive-bonding). While arthroplasty jigs with one positioning component have been described, some arthroplasty jigs may include multiple positioning components, such as two, three, four, five, or ten positioning components. The positioning components may be the same type of positioning component, or different types of positioning components. As an example, an arthroplasty jig may include both a positioning component in the form of a projection having a pointed end, and a positioning component in the form of a projection having a rounded end.

Figure 6A:
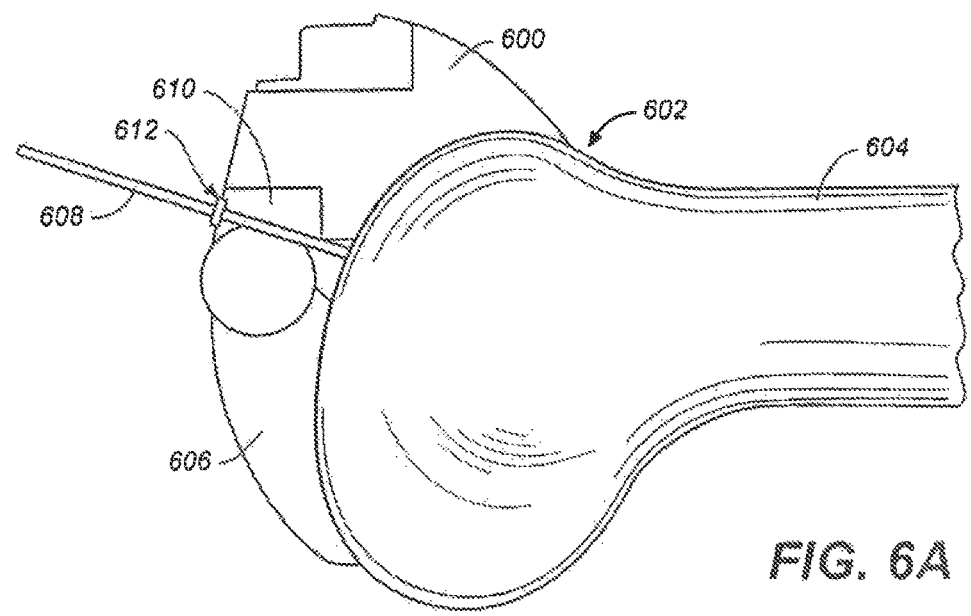
FIG. 6A is an illustration of a portion of a femur of a subject, and an arthroplasty jig aligned with the portion of the femur.
Figure 6B:
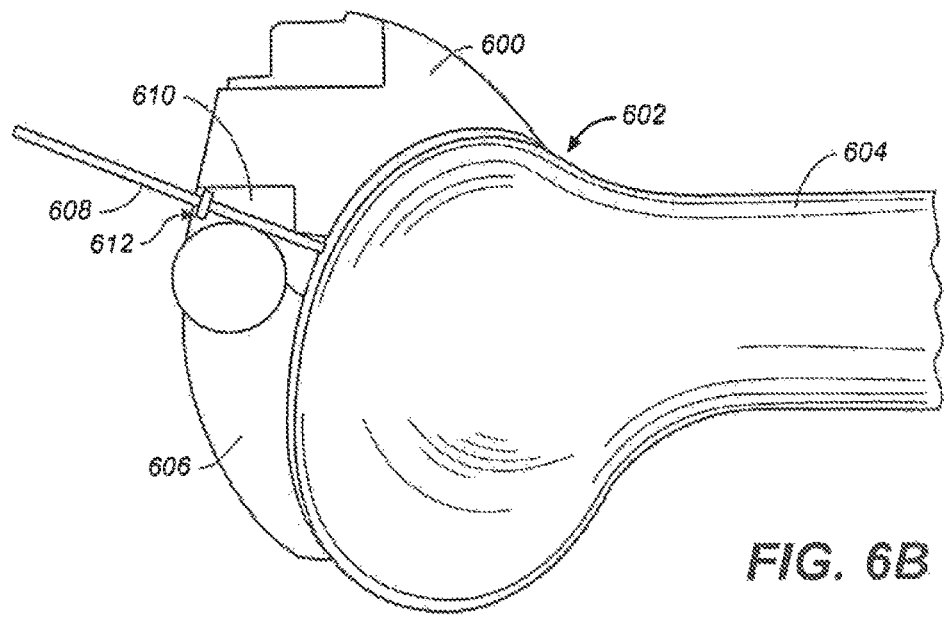
FIG. 6B is an illustration of the portion of the femur of FIG. 6A, when the arthroplasty jig of FIG. 6A is not aligned with the portion of the femur.

In some variations, an arthroplasty jig may include one or more positioning components that are neither integrally formed with, nor permanently attached to, its jig body. As an example, FIG. 6A shows an arthroplasty jig (600) that is aligned with a distal end (602) of a femur (604). Arthroplasty jig (600) includes a jig body (606) and a positioning component (as shown, a rod (608)) extending through an aperture (610) in jig body (606). A collar (612) surrounds rod (608), and may be used by a physician to determine whether arthroplasty jig (600) has been correctly positioned and aligned on distal end (602) of femur (604). More specifically, when the physician is positioning arthroplasty jig (600) on femur (604), the physician may advance rod (608) through aperture (610), until rod (608) contacts a surface of femur (604). At this point, the physician can check the position of collar (612), which will indicate whether arthroplasty jig (600) is in the correct position. If collar (612) is just outside of aperture (610), as shown in FIG. 6A, then arthroplasty jig (600) is correctly aligned. By contrast, if collar (612) is either not visible or not just outside of aperture (610), then the physician knows that arthroplasty jig (600) is not yet correctly aligned. For example, FIG. 6B shows arthroplasty jig (600) when it is not correctly aligned with femur (604). Collar (612) is disposed within aperture (610), thereby indicating that proper alignment has not yet been achieved.

In certain variations, collar (612) may be a different color from rod (608) and/or jig body (606). For example, rod (608) may be black and jig body (606) may be white, while collar (612) is green. This difference in color may enhance the visibility of collar (612), which may, in turn, enhance the ability of a physician to readily determine whether arthroplasty jig (600) is correctly aligned with femur (604).

Moreover, while FIGS. 6A and 6B show a rod and a collar, other types of positioning components may be used. As an example, a rod may include measurement markings (e.g., millimeter markings) that allow a physician to determine how deeply the rod has advanced into an aperture in a jig body. In certain variations, the rod may also include a collar or one or more other types of markers. Furthermore, in some variations, an arthroplasty jig may include one or more pins, springs, and/or wires (e.g., as an alternative to a rod or in addition to a rod). In certain variations, a positioning component may not be disposed within an aperture of a jig body. For example, an arthroplasty jig may include a jig body and a positioning component, such as a rod, which is movably attached to an outer surface of the jig body.

Arthroplasty jigs may have other positioning components that can provide a physician with a tactile indication of correct alignment. Additional examples of arthroplasty jigs that provide a physician with a tactile indication of correct alignment are described with reference to FIGS. 7A-9.

FIG. 7A shows a femur (700) having a distal end (702) and a lock (704) secured to distal end (702). In some variations, lock (704) may be temporarily secured to distal end (702) using, for example, an adhesive. FIG. 7A also shows an arthroplasty jig (706) including a jig body (708) having two slots (710) and (712), and a projection (714) extending from jig body (708). In FIG. 7A, arthroplasty jig (706) is being positioned so that projection (714) faces lock (704). FIG. 7B shows arthroplasty jig (706) when projection (714) has been locked or snapped into lock (704), and jig body (708) has been aligned with a surface (718) of femur (700). The sensation of projection (714) locking or snapping into lock (704) may provide a physician with a tactile indication that arthroplasty jig (706) has been correctly positioned for alignment with surface (718) of femur (700). Furthermore, there may be a sound associated with projection (714) locking or snapping into lock (704), which can provide a physician with an audible indication that arthroplasty jig (706) has been correctly positioned for alignment with surface (718) of femur (700). Additionally, by locking or snapping projection (714) into lock (704), a physician can temporarily secure jig body (708) to femur (700), so that jig body (708) may exhibit little or no movement during the arthroplasty procedure.

FIGS. 8A and 8B show another type of arthroplasty jig that may provide a tactile indication when correct alignment has been achieved at a target site. In FIG. 8A, an arthroplasty jig (800) including a jig body (802) having two slots (804) and (806) is being positioned on a distal end (808) of a femur (810). Jig body (802) may be formed of, for example, one or more shape-memory and/or superelastic materials that can allow the jig body to be temporarily deformed around the distal end of the femur. Jig body (802) also includes two claw-shaped positioning components (812) and (814). In FIG. 8B, arthroplasty jig (800) has been aligned with a surface (816) of femur (810). Claw-shaped positioning components (812) and (814) help to temporarily secure arthroplasty jig (800) to femur (810), which may thereby limit or prevent movement of the arthroplasty jig during an arthroplasty procedure. As arthroplasty jig (800) aligns with surface (816) of femur (810), a physician may sense arthroplasty jig (800) returning to its original configuration (i.e., its configuration prior to deformation), as well as claw-shaped positioning components (812) and (814) securing to femur (810). Furthermore, the physician may perceive that it is more difficult to move arthroplasty jig (800) once it has been aligned with surface (816) of femur (810).

Figure 9:
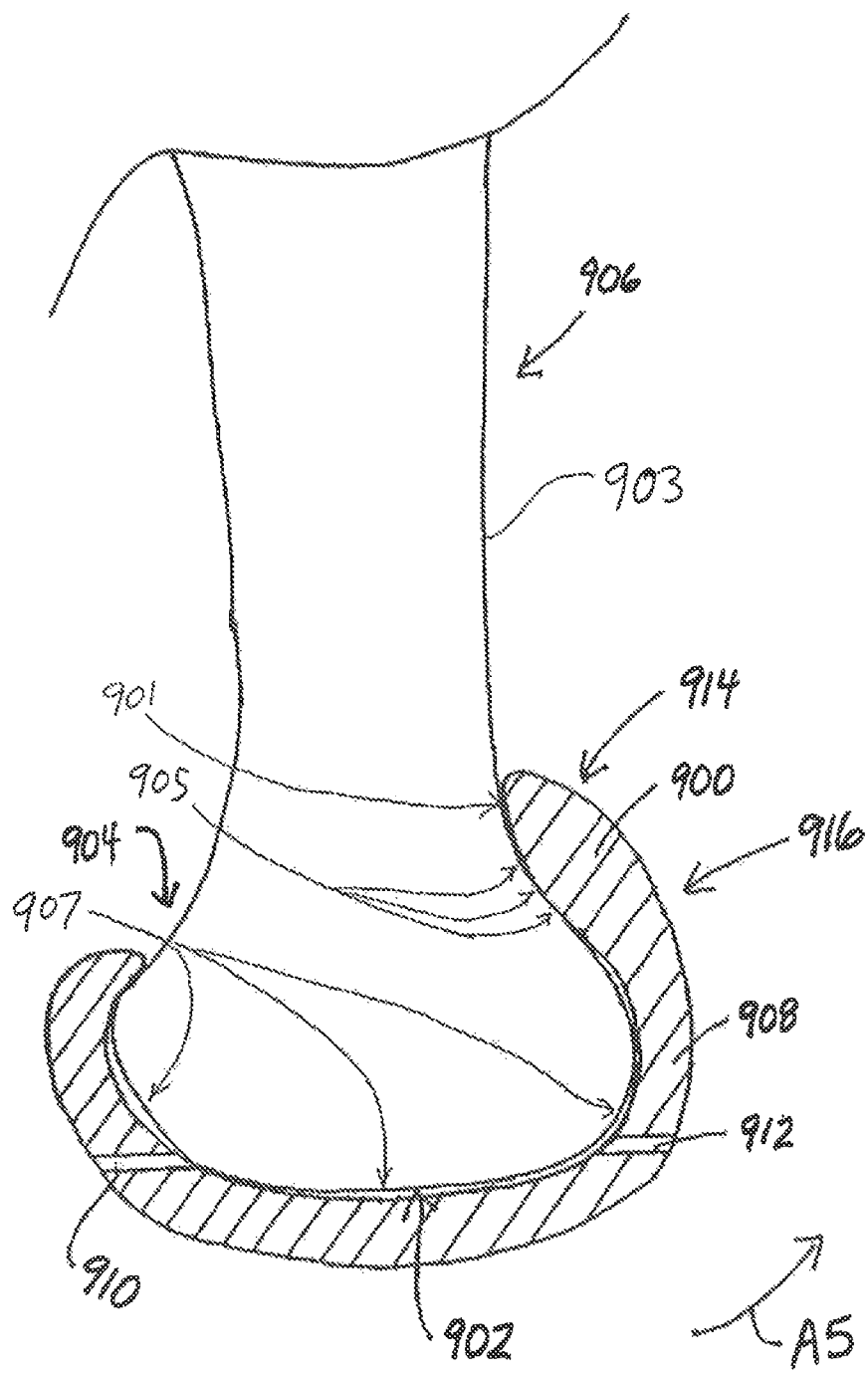
FIG. 9 is an illustration of a portion of a femur of a subject, and an arthroplasty jig aligned with the portion of the femur.

Certain variations of arthroplasty jigs may include one or more stops that help in the positioning and alignment of the arthroplasty jigs at a target site. For example, FIG. 9 shows an arthroplasty jig (900) that is aligned with a surface (902) of a distal end (904) of a femur (906). Arthroplasty jig (900) includes a jig body (908) with two slots (910) and (912), and a positioning component in the form of a stop (914) located at one of the ends (916) of jig body (908). The stop (914) may contact a femur surface, such as, for example, a surface (901) of the femur shaft (903) and a surface (905) for a transition region between the femoral shaft (903) and the condyle region (907) of the femoral distal end (904). As a physician is positioning arthroplasty jig (900) on femur (906), the physician may perceive contact between stop (914) and femur (906) when arthroplasty jig (900) becomes aligned with surface (902) of distal end (904) of femur (906). This tactile perception can provide an indication to the physician that alignment has been achieved, so that the physician no longer needs to adjust the position of the arthroplasty jig. Furthermore, the stop may even prevent the physician from further adjusting arthroplasty jig (900) in the direction of arrow (A5).

Figure 10A:
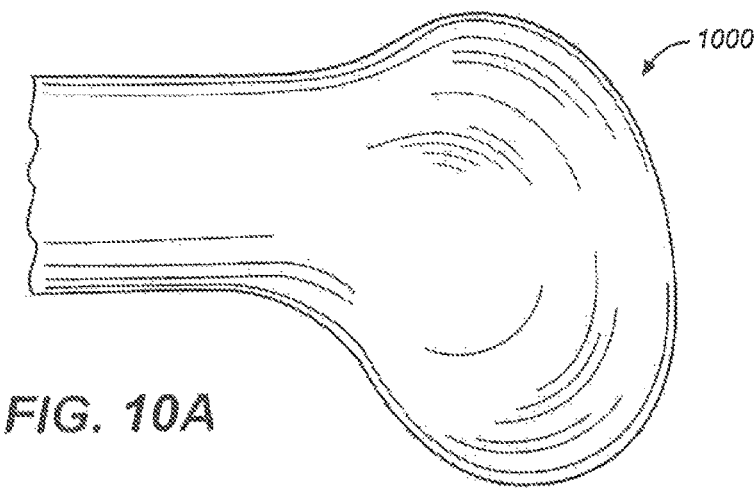
FIG. 10A is an illustration of a portion of a femur of a subject.
Figures 10B, 10C:
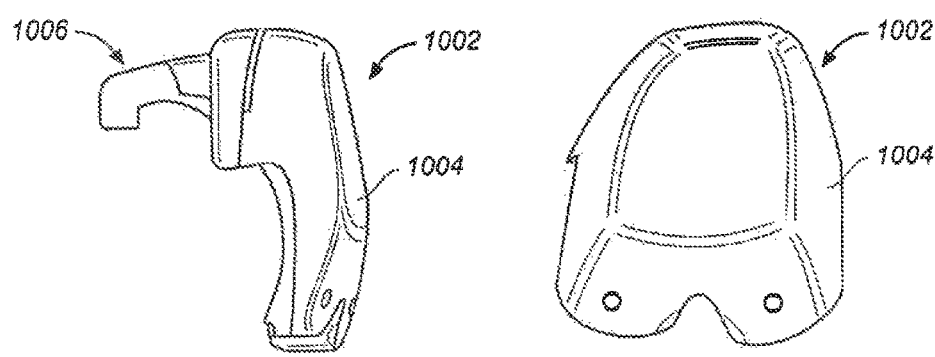
FIG. 10B is a front view of an arthroplasty jig.
FIG. 10C is a side view of the arthroplasty jig of FIG. 10B.
Figure 10D:
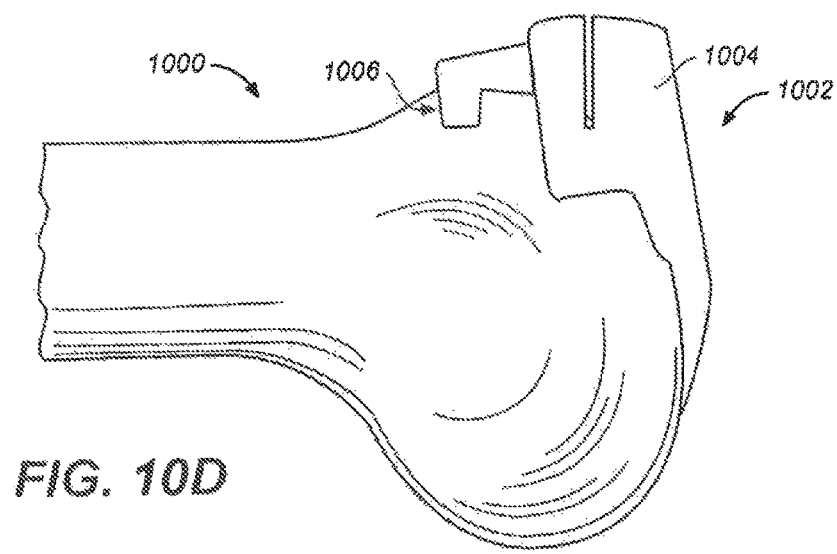
FIG. 10D is an illustration of the arthroplasty jig of FIGS. 10B and 10C, after it has been aligned with the portion of the femur of FIG. 10A.

In some variations, an arthroplasty jig may include one or more hook-shaped positioning components that can provide a tactile indication of proper positioning and alignment of the arthroplasty jig at a target site. For example, FIG. 10A shows a distal portion of a femur (1000), and FIGS. 10B and 10C show front and side views, respectively, of an arthroplasty jig (1002) configured for use with femur (1000). As shown in FIGS. 10B and 10C, arthroplasty jig (1002) includes a jig body (1004) and a hook-shaped positioning component (1006) extending from jig body (1004). As FIG. 10D shows, hook-shaped positioning component (1006) may be used to engage arthroplasty jig (1002) with femur (1000). For example, hook-shaped positioning component (1006) may be configured to temporarily latch onto one or more osteophytes on femur (1000), and/or to engage with cartilage.

While the above-described arthroplasty jigs are configured to provide a physician with a tactile indication of correct alignment, certain variations of arthroplasty jigs may alternatively or additionally provide one or more other types of indications of correct alignment. As an example, and as discussed above with reference to FIGS. 7A and 7B, an arthroplasty jig may provide an audible indication when its jig body has been properly positioned at a target site. While a snapping or locking sound has been described, in some variations, an arthroplasty jig may emit a different kind of sound. For example, in certain variations, an arthroplasty jig may include a sensor that, upon contacting a bone surface, triggers the emission of an audible signal, such as a temporary beeping sound. This beeping sound can be used to notify the physician that the arthroplasty jig has been properly positioned. As another example, and as discussed above with reference to FIGS. 3A and 3B, an arthroplasty jig may provide a visible indication when it has been properly positioned. An example of a visible indication is a flashing light, although other visual indications may be used. The visible indication may be activated by, for example, a sensor that has contacted a bone surface.

Figure 11A:
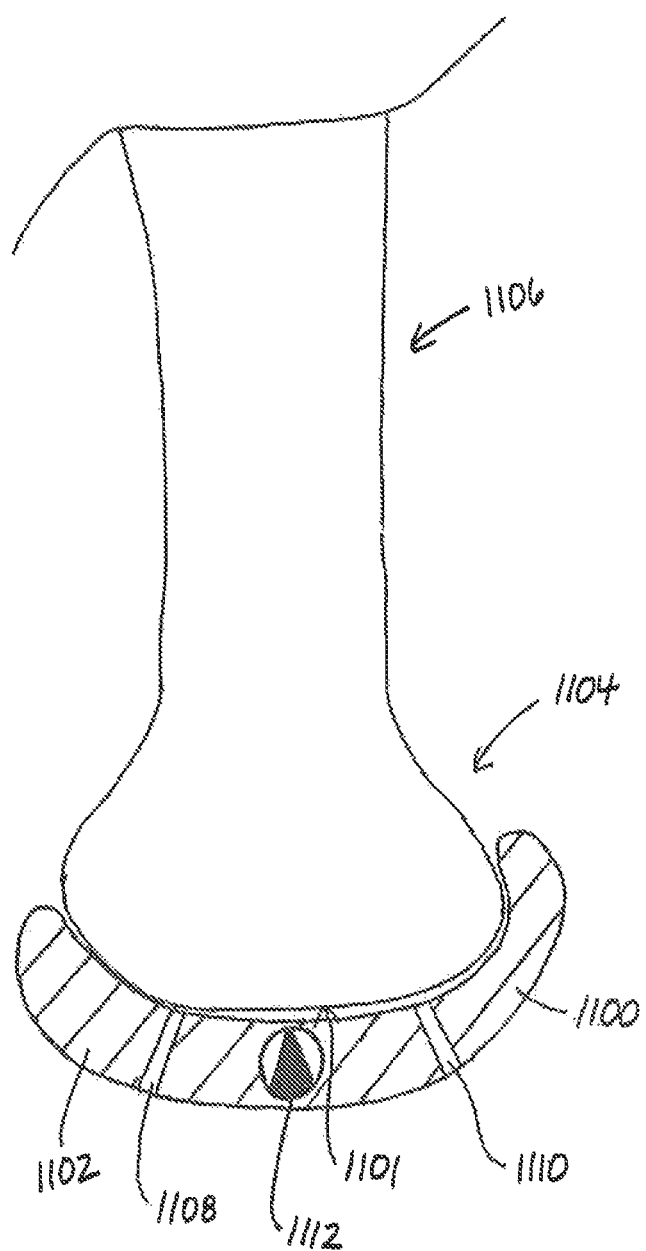
FIG. 11A is an illustration of a portion of a femur of a subject, and an arthroplasty jig aligned with the portion of the femur.
Figure 11B:
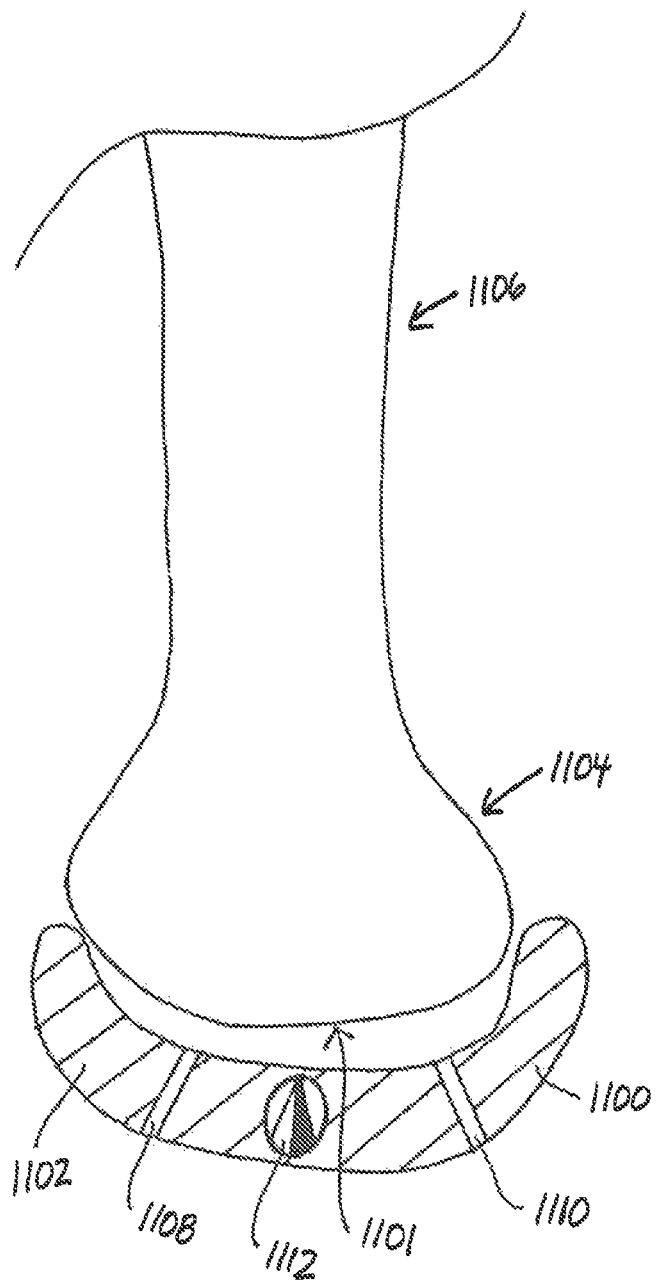
FIG. 11B is an illustration of the portion of the femur of FIG. 11A, when the arthroplasty jig of FIG. 11A is not aligned with the portion of the femur.
Figure 12:
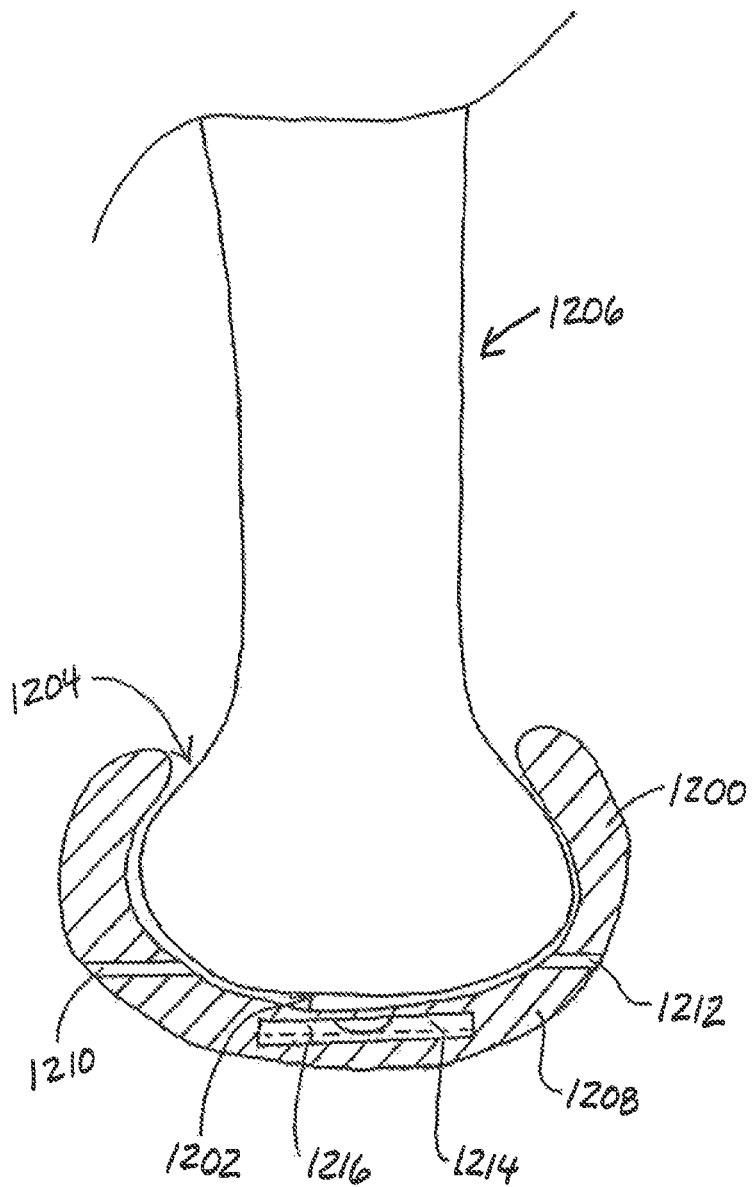
FIG. 12 is an illustration of a portion of a femur of a subject, and an arthroplasty jig aligned with the portion of the femur.

Additional examples of arthroplasty jigs that provide a visible indication of proper positioning and alignment are shown in FIGS. 11A-12. FIG. 11A shows an arthroplasty jig (1100) that is aligned with a surface (1101) of a distal end (1104) of a femur (1106). Arthroplasty jig (1100) includes a jig body (1102) with two slots (1108) and (1110) and an alignment indicator (1112). Because arthroplasty jig (1100) is properly aligned with surface (1101) in FIG. 11A, alignment indicator (1112) displays a full black triangle. However, and as shown in FIG. 11B, when arthroplasty jig (1100) is not properly aligned with surface (1101), the triangle in alignment indicator (1112) is no longer entirely black but rather, a combination of black and white (or another color). Alignment indicator (1112) may be formed of, for example, a black plate and a white plate that can shift into different positions relative to each other, depending on the position of arthroplasty jig (1100). FIG. 12 shows an arthroplasty jig (1200) that is aligned with a surface (1202) of a distal end (1204) of a femur (1206). Arthroplasty jig (1200) includes a jig body (1208) having two slots (1210) and (1212), and a level (1214). Because arthroplasty jig (1200) is aligned with surface (1202), the fluid (1216) in level (1214) indicates that the arthroplasty jig is level. However, if arthroplasty jig (1200) were not aligned with surface (1202), then the fluid would indicate that the arthroplasty jig was not level.

As discussed above, other methods of correctly identifying an arthroplasty jig and positioning the arthroplasty jig at a target site may be used, either in conjunction with one or more of the above-described methods, or as an alternative to one or more of the above-described methods.

One example of such a method is the inclusion of identifying information on an arthroplasty jig. The presence of the identifying information on the arthroplasty jig may reduce the likelihood of the wrong arthroplasty jig being selected for use during a particular arthroplasty procedure. In some variations, the presence of identifying information on an arthroplasty jig may result in reduced procedure time. For example, it may allow a physician to readily confirm that the correct arthroplasty jig has been selected for a particular patient or procedure.

The identifying information may include any type of information that is useful on a medical device. For example, the identifying information may include patient data (e.g., a patient's name, date of birth, weight, height, allergies, etc.), doctor information, surgery information (e.g., date of surgery, hospital at which surgery is to take place, etc.), information regarding the size and/or materials of the jig body, company logos, barcodes, etc. In some variations, the identifying information may provide specific information about a target site, and/or may help a physician to position the arthroplasty jig. For example, the arthroplasty jig may include markings such as "femur," "tibia," "left knee," "right knee," "this side up," "this side down," and/or any other appropriate markings. In certain variations, an arthroplasty jig may include markings that provide one or more of the dimensions of the arthroplasty jig, such as the length, width, or thickness of the arthroplasty jig. Other examples of markings may include markings that help a physician to make measurements, such as millimeter markings. Any number of different markings may be used on an arthroplasty jig, and the examples provided here are not intended to be limiting.

Identifying information may be added onto a jig body in any of a number of different ways. For example, the identifying information may be printed onto, and/or engraved (e.g., etched, cut, or carved) into, the jig body, and/or may be located on one or more adhesive labels that are affixed to the jig body. Any other methods of marking an arthroplasty jig with one or more biocompatible markings may also be used. An arthroplasty jig may include just one marking, or multiple markings. The markings may be the same color or different colors, and may be in the same font or different fonts. Furthermore, while arthroplasty jigs that are marked with identifying information have been described, certain variations of arthroplasty jigs may include other types of markings. As an example, certain variations of arthroplasty jigs may include aesthetic markings, such as designs.

In some variations, identifying information may be provided on a tag (e.g., a metal tag) that is temporarily attached to the arthroplasty jig. The identifying information may, for example, be engraved into the tag. The arthroplasty jig itself may or may not also be marked with identifying information. The metal tag may be removed (e.g., by a physician) prior to the arthroplasty jig being used in an arthroplasty procedure.

Figure 13:
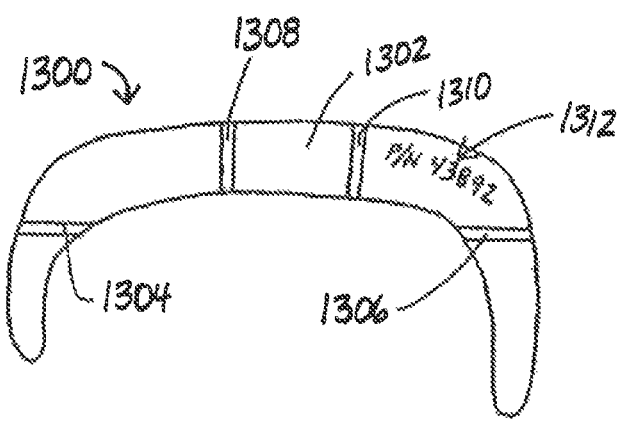
FIG. 13 is an illustration of an arthroplasty jig.
Figure 14:
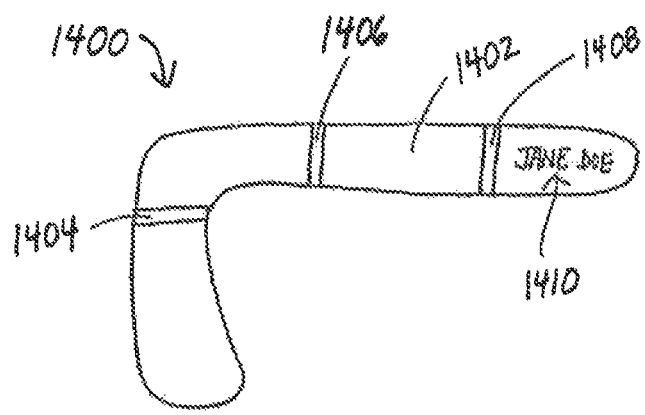
FIG. 14 is an illustration of an arthroplasty jig.

FIGS. 13 and 14 show examples of arthroplasty jigs that are marked with identifying information. As shown in FIG. 13, a femoral arthroplasty jig (1300) includes a jig body (1302) having two slots (1304) and (1306) and two apertures (1308) and (1310). Identifying information (1312) (as shown, a part number) is marked on jig body (1302). Similarly, FIG. 14 shows a tibial arthroplasty jig (1400) including a jig body (1402) having a slot (1404) and two apertures (1406) and (1408). Jig body (1402) is marked with identifying information (1410) (as shown, a patient name).

Arthroplasty jigs may be formed using any of a number of different procedures. In some variations, arthroplasty jigs may be formed from one or more arthroplasty jig blanks. The arthroplasty jig blanks that are used to form arthroplasty jigs may have different sizes and/or shapes. For example, some arthroplasty jig blanks may be designed for use with the left side of a patient's body (e.g., a left knee), while other arthroplasty jig blanks are designed for use with the right side of a patient's body (e.g., the right knee). In certain variations, an arthroplasty jig blank may be marked (e.g., using one or more of the marking methods described above with reference to arthroplasty jigs).

The arthroplasty jigs and jig blanks described herein may be formed of any of a number of different materials. They may be formed of just one material, or multiple materials, such as a blend of different materials or layers of different materials. Examples of suitable materials include polymers, metals, ceramics, metal alloys, and combinations thereof. Specific examples of polymers include acetal resins (e.g., Delrin®), polyetheretherketones (PEEK), polycarbonates, polyamides, polyesters, polystyrenes, polyacrylates, vinyl polymers, and polyurethanes. Specific examples of metals and metal alloys include gold, platinum, palladium, stainless steel, cobalt alloys (e.g., Elgiloy®), and nickel-titanium alloys (e.g., Nitinol™). In some variations, the arthroplasty jig blanks may be formed of one or more plastics. In such variations, the blanks may be formed, for example, using injection molding technology and/or thermal plastic press forming technology. In certain variations, an arthroplasty jig may be intended to be disposable, while in other variations, an arthroplasty jig may be intended to be reusable. The materials out of which an arthroplasty jig is formed may be selected with these and/or other criteria in mind. Moreover, certain variations of arthroplasty jigs may be formed of two or more layers of different materials, and/or may include one or more coatings.

In some variations, arthroplasty jigs may be customized so that the accuracy of their positioning and alignment (and, therefore, the accuracy with which they position and align instruments) may be enhanced. Various methods may be used to form customized arthroplasty jigs, such as the methods described, for example, in U.S. patent application Ser. No. 10/146,862, filed on May 15, 2002, which is hereby incorporated by reference in its entirety.

Figure 15:
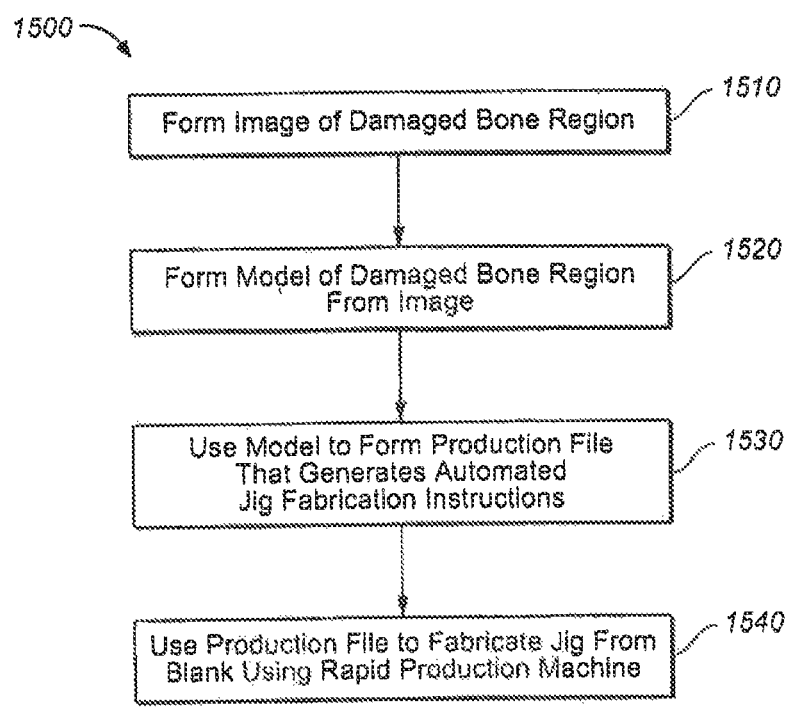
FIG. 15 is a flowchart representation of a method of forming an arthroplasty jig.

One variation of a method (1500) that may be used to form customized arthroplasty jigs is depicted as a flowchart in FIG. 15. As shown in FIG. 15, this illustrative method comprises forming an image of a damaged bone region of a patient (1510) using, for example, computer tomography (CT) and/or magnetic resonance imaging (MRI). The image may be formed specifically of the damaged bone region, or may include portions of the bone that are not damaged. As an example, an image of a damaged knee region may include the entirety of the knee region, as well as the entirety of the associated femur and tibia. After the image has been formed, a three-dimensional model of the damaged bone region is formed from the image (1520). The model may be formed, for example, by using the image to determine location coordinate values of each of a sequence of spaced apart surface points in the damaged bone region, and then using a mathematical model to estimate or compute the three-dimensional model. Thereafter, the model and the image are used to generate a production file that provides automated arthroplasty jig fabrication instructions (1530) to a rapid production machine. The rapid production machine then fabricates a customized arthroplasty jig from an arthroplasty jig blank according to the instructions (1540).

While one method of manufacturing a customized arthroplasty jig has been described above, other methods may be used. For example, one-, two-, and three-dimensional measurements of a target site may be taken using lasers, electromagnetic or optical tracking systems, or other imaging methods. As an example, while CT and MRI have been described, other imaging methods that may be used include X-ray technology, optical coherence tomography, ultrasound imaging, and optical imaging. In some variations, multiple imaging techniques may be used together to image a target site. Moreover, the measurements that are used to image an area may be taken in a non-invasive manner, or may be taken intra-operatively (e.g., using optical, mechanical, and/or ultrasound probes). Additionally, while customized arthroplasty jigs have been described, some variations of arthroplasty jigs may not be customized for a particular patient.

While methods and devices described herein have been described with respect to arthroplasty jigs, in some variations, one or more features of the methods and devices described above may be applied to implants, such as arthroplasty implants. Moreover, while arthroplasty procedures have been described, the jigs and implants described herein may be used in any of a number of different procedures, including, for example, spinal surgery.

While the methods, devices, and apparatuses have been described in some detail here by way of illustration and example, such illustration and example is for purposes of clarity of understanding only. It will be readily apparent to those of ordinary skill in the art in light of the teachings herein that certain changes and modifications may be made thereto without departing from the spirit and scope of the pending claims.

The invention claimed is:

1. A customized arthroplasty jig for facilitating an arthroplasty procedure on a bone of a patient, the bone having a joint region, a shaft extending away from the joint region and a transition region between the joint region and the shaft, the joint region having an associated surface of at least one of cartilage or bone, the jig comprising:
   a jig body of unitary construction and comprising:
      a patient-specific jig surface configured to at least one of align with or position on the associated surface in a customized fashion, the patient-specific jig surface existing in the jig body prior to coming into contact with the associated surface, the patient-specific jig surface manufactured in a customized configuration particular to the associated surface of the patient;

a positioning component extending from the patient-specific jig surface and configured to contact the transition region or the shaft when the patient-specific jig surface is positioned on the associated surface in the customized fashion; and a first aperture extending through the jig body and configured to guide the placement of a first pin into the bone.

2. The jig of claim 1, wherein the bone is that of a femur.

3. The jig of claim 2, wherein the joint region is a knee region.

4. The jig of claim 1, wherein the bone is that of a tibia.

5. The jig of claim 4, wherein the joint region is a knee region.

6. The jig of claim 1, wherein the joint region is one of a hip region, shoulder region, or elbow region.

7. The jig of claim 1, wherein the first pin is configured to secure the jig body to the bone.

8. The jig of claim 1, wherein the patient-specific jig surface is at least a result of a manufacturing process including: forming at least one image of the joint region; forming a three-dimensional model of the joint region from the at least one image; and generating the patient-specific jig surface based at least in part on data determined from the three-dimensional model.

9. The jig of claim 1, wherein the jig body further comprises a resection slot configured to guide a planar resection in the bone.

10. The jig of claim 1, wherein the arthroplasty jig includes identifying information present on the jig body, the identifying information associated with at least one of the patient or a medical professional.

11. The jig of claim 10, wherein the identifying information is engraved into the jig body.

12. The jig of claim 10, wherein the identifying information is printed onto the jig body.

13. The jig of claim 10, wherein the identifying information is provided on a label that is affixed to the jig body.

14. The jig of claim 10, wherein the identifying information includes at least one of a patient name, a number associated with the patient, an identification of the bone, or an identification of the joint region.

15. The jig of claim 1, wherein the jig body further comprises a second aperture configured to receive a rod therethrough, wherein, when the rod is positioned in the second aperture, the rod is configured to determine correct positioning of the patient-specific jig surface on the associated surface.

16. The jig of claim 15, wherein the rod comprises a collar, and wherein a position of the collar relative to the second aperture determines correct positioning of the patient-specific jig surface on the associated surface.

17. The jig of claim 1, wherein the jig body further comprises a second aperture configured to receive a rod therethrough, wherein, when the rod is positioned in the second aperture, the jig body and the rod are configured to be moved together on the bone until the patient-specific jig surface is correctly positioned on the associated surface.

18. The jig of claim 17, wherein a position of the rod determines when the patient-specific jig surface is correctly positioned on the associated surface.

19. The jig of claim 1, wherein the jig body further comprises an alignment indicator configured to provide visual indication that the patient-specific jig surface is correctly aligned with the associated surface.

20. The jig of claim 19, wherein the alignment indicator is configured to indicate when the jig body is in a level orientation.

21. The jig of claim 19, wherein the alignment indicator comprises a level.

22. The jig of claim 1, wherein the jig body further comprises an alignment indicator configured to provide visual indication that the jig body is in a level orientation.

23. The jig of claim 22, wherein the alignment indicator comprises a level.

* * * * *